(12) United States Patent
Dalen et al.

(10) Patent No.: US 6,548,486 B1
(45) Date of Patent: Apr. 15, 2003

(54) FATTY ACID ESTERS OF NUCLEOSIDE ANALOGS

(75) Inventors: Are Dalen, Trondheim (NO); Finn Myhren, Porsgrunn (NO); Bernt Børretzen, Heistad (NO); Kjell Torgeir Stokke, Oslo (NO)

(73) Assignee: Norsk Hydro a.s., Oslo (NO)

( * ) Notice: Subject to any disclaimer, the term of this patent is extended or adjusted under 35 U.S.C. 154(b) by 0 days.

(21) Appl. No.: 08/211,386

(22) PCT Filed: Sep. 30, 1992

(86) PCT No.: PCT/NO92/00162

§ 371 (c)(1),
(2), (4) Date: Sep. 21, 1994

(87) PCT Pub. No.: WO93/07163

PCT Pub. Date: Apr. 15, 1993

(30) Foreign Application Priority Data

Oct. 7, 1991 (GB) ............................................. 9121257

(51) Int. Cl.[7] ........................ A61K 31/70; C07H 19/02; C07H 19/06; C07H 19/16
(52) U.S. Cl. ............................. 514/43; 514/45; 514/46; 514/49; 514/50; 514/261; 514/262; 536/28.54; 536/27.6; 544/276; 544/277
(58) Field of Search .............................. 536/28.54, 27.6; 514/45, 46, 49–50, 262, 261, 43; 544/276, 277

(56) References Cited

U.S. PATENT DOCUMENTS

| | | | |
|---|---|---|---|
| 3,920,630 A | 11/1975 | Wechter et al. | 260/211.5 R |
| 4,740,503 A | 4/1988 | Hori et al. | 514/51 |
| 4,816,447 A | 3/1989 | Ashton et al. | 514/81 |
| 5,216,142 A | 6/1993 | Horrobin et al. | 514/50 |
| 5,250,535 A | 10/1993 | Verheyden et al. | 514/262 |
| 5,276,020 A | 1/1994 | Horrobin et al. | 514/45 |

FOREIGN PATENT DOCUMENTS

| | | |
|---|---|---|
| EP | 0056265 | 7/1982 |
| EP | 0066208 | 12/1982 |
| EP | 0074306 | 3/1983 |
| EP | 0085424 | 8/1983 |
| EP | 0105135 | 4/1984 |
| EP | 0165164 | 12/1985 |
| EP | 0393920 | 10/1990 |
| JP | 57-62294 | 4/1982 |
| JP | 61-171498 | 8/1986 |
| JP | 64-83092 | 3/1989 |
| JP | 2-78696 | 3/1990 |
| WO | 8903838 | * 5/1989 |
| WO | WO9000555 | 1/1990 |

OTHER PUBLICATIONS

Ozaki, et al., "5–Fluorouracil Derivatives", Chemical and Pharmaceutical Bulletin, vol. 38, No. 11, pp. 3164–3166 (1990).

Rubas et al. "Treatment of Murine L1210 Lymphoid Leukemia and Melanoma B16 with . . ." Int. J. Cancer: 37, pp. 149–154 (1986).

Hamamura et al. "Reactions of 2–Acyloxyisobutyl Halides with Nucleosides . . ." J. Med. Chem. vol. 19. No. 5, pp. 667–674 (1976).

* cited by examiner

*Primary Examiner*—Gary L. Kunz
(74) *Attorney, Agent, or Firm*—Fitzpatrick, Cella, Harper & Scinto

(57) ABSTRACT

New compounds of the general formula (I): Nu-O-Fa, wherein O represents an oxygen, Nu is a nucleoside or nucleoside analogue, and Fa is an acyl group of a mono-unsaturated C18 or 20 fatty acid. The invention also concerns anti viral pharmaceutical and veterinary compositions comprising a compound of formula (I) alone in a combination with a pharmaceutically acceptable carrier.

43 Claims, 14 Drawing Sheets

1: CONTROL, 2: ACV, 3: ACV-LINOLENATE, 4: ACV-ERUCATE, 5: ACV-OLEATE, 6: ACV-ELAIDATE, 7: ACV-EICOSENATE

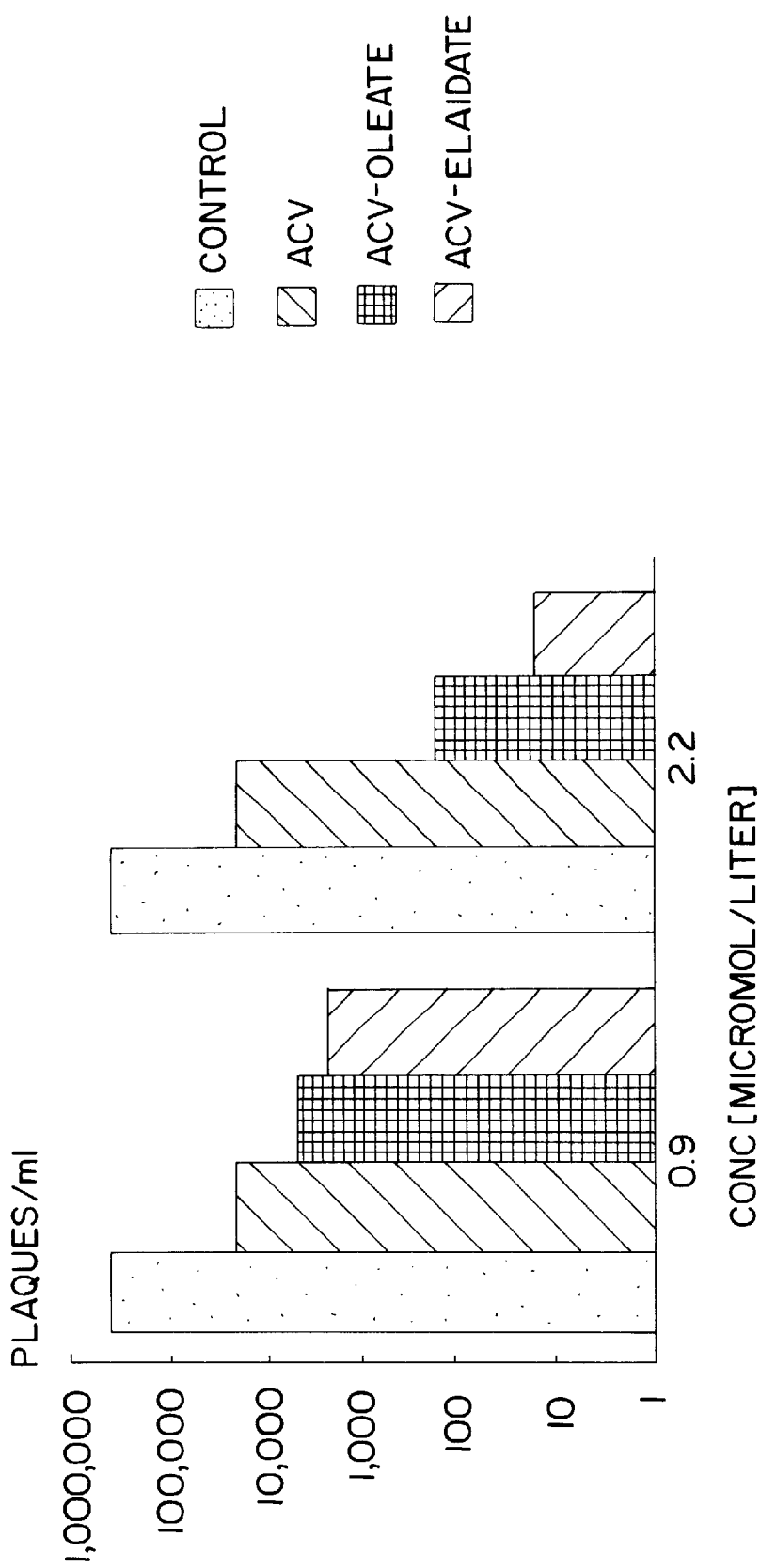

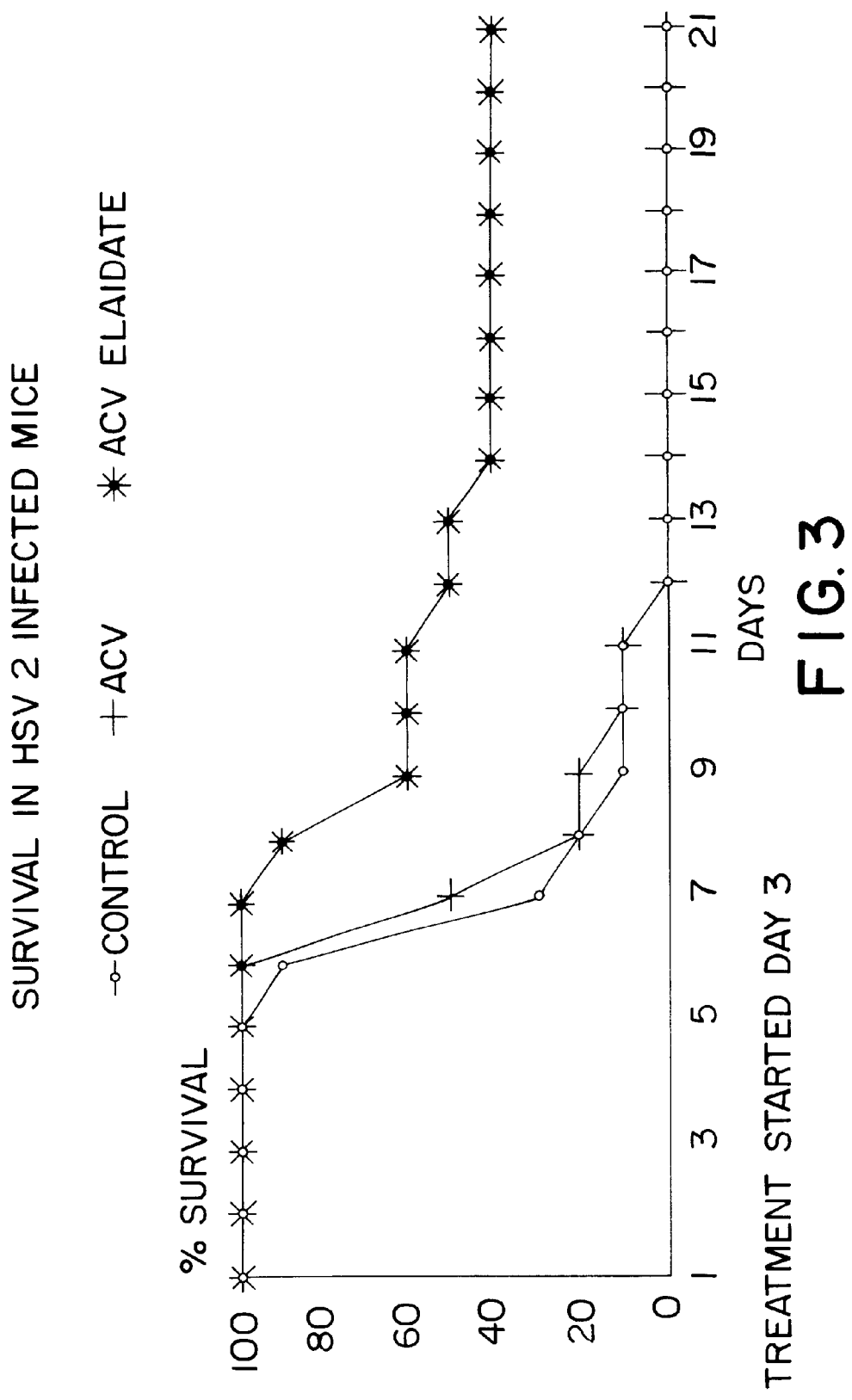

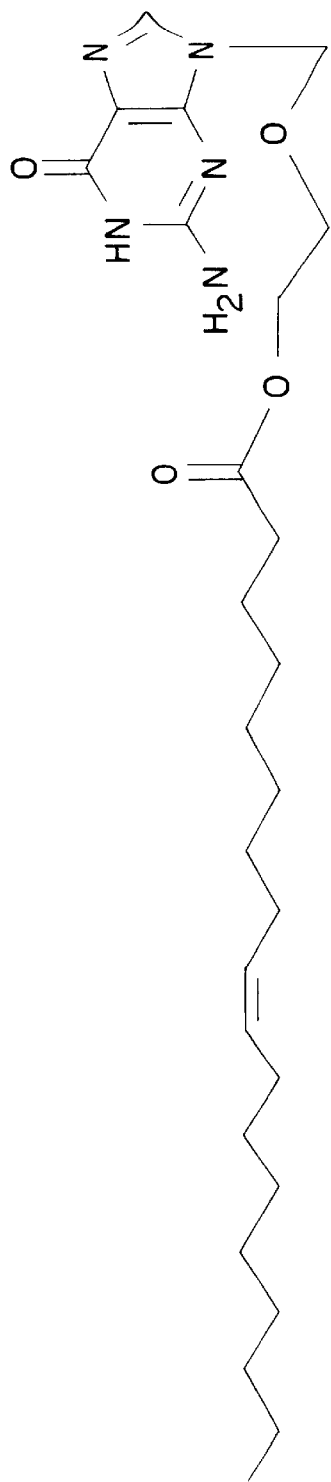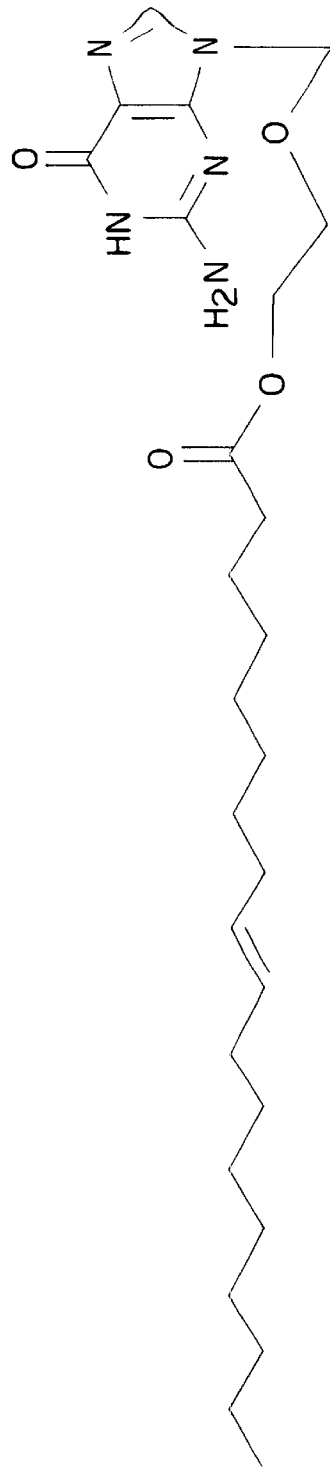
FIG. 4A ACV OLEATE
FIG. 4B ACV ELAIDATE

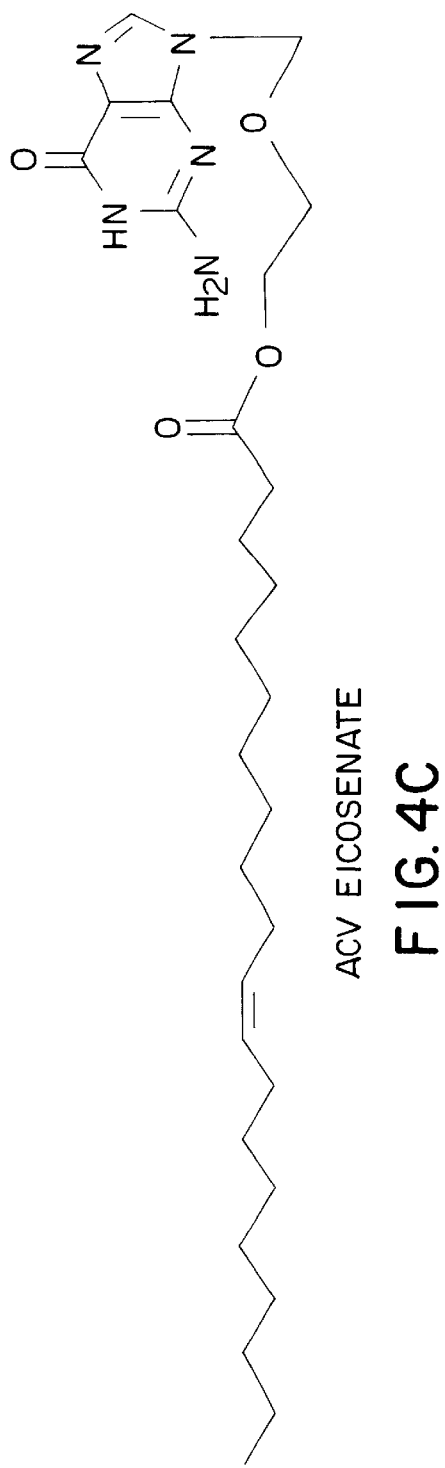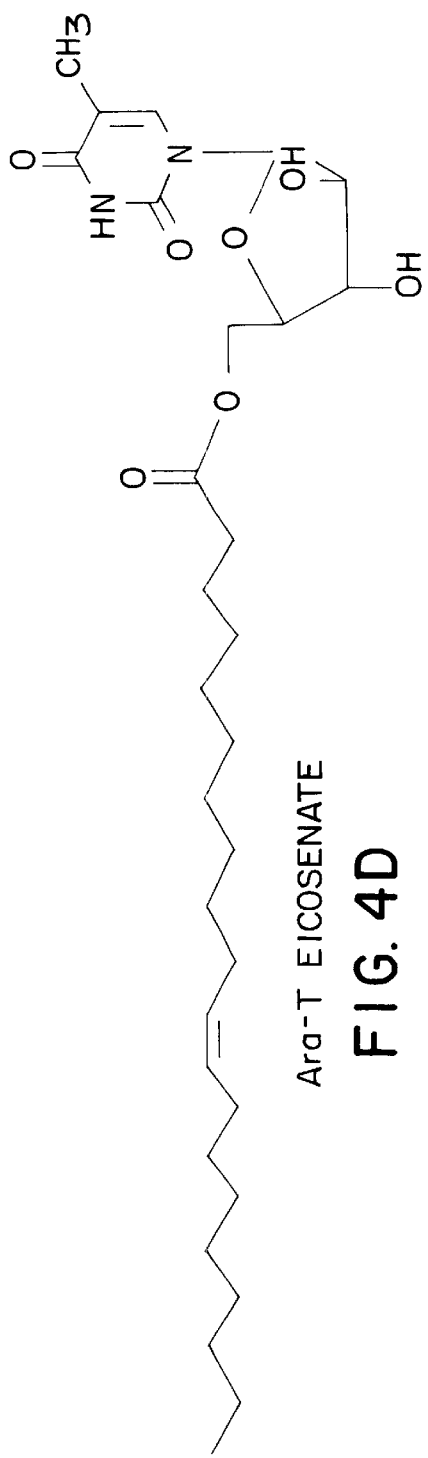
ACV EICOSENATE
FIG. 4C
Ara-T EICOSENATE
FIG. 4D

Ara-T OLEATE

Ara-T ELAIDATE

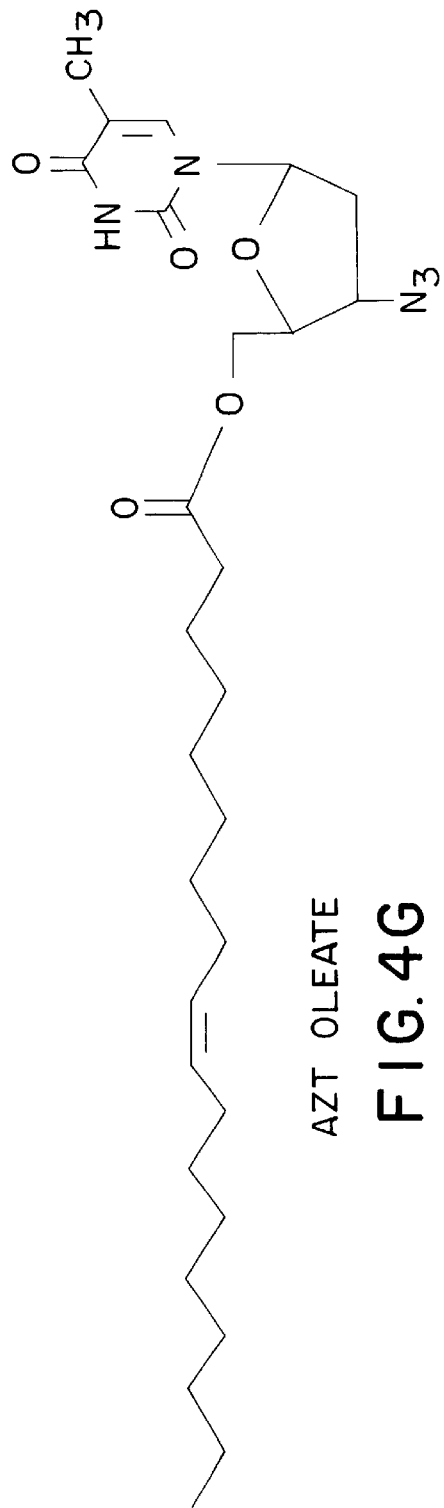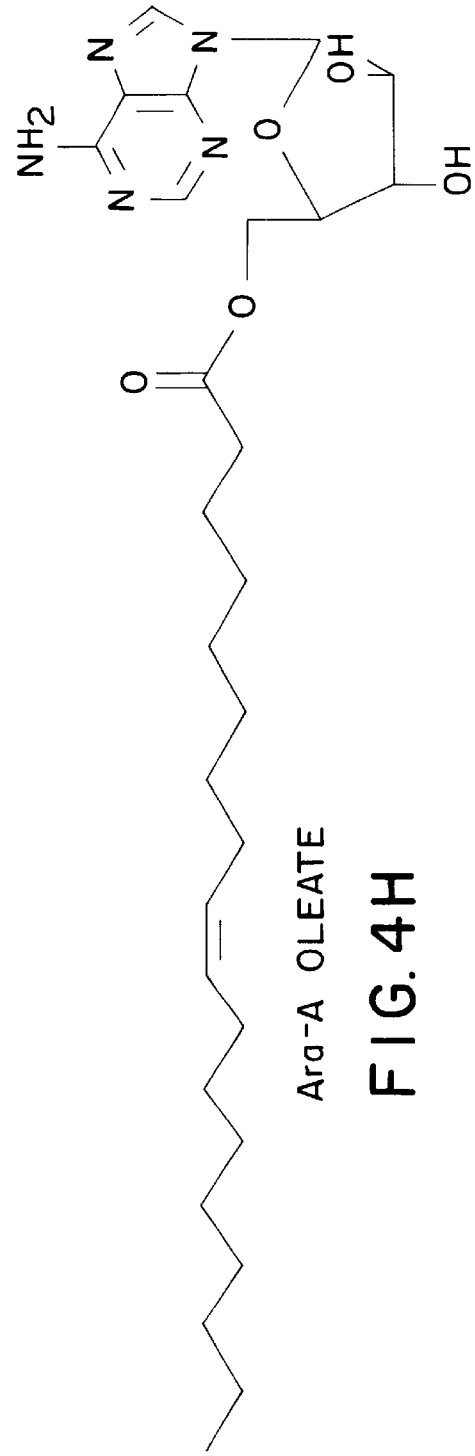
AZT OLEATE
FIG. 4G
Ara-A OLEATE
FIG. 4H

Ara-A ELAIDATE

Ara-A EICOSENATE, cis

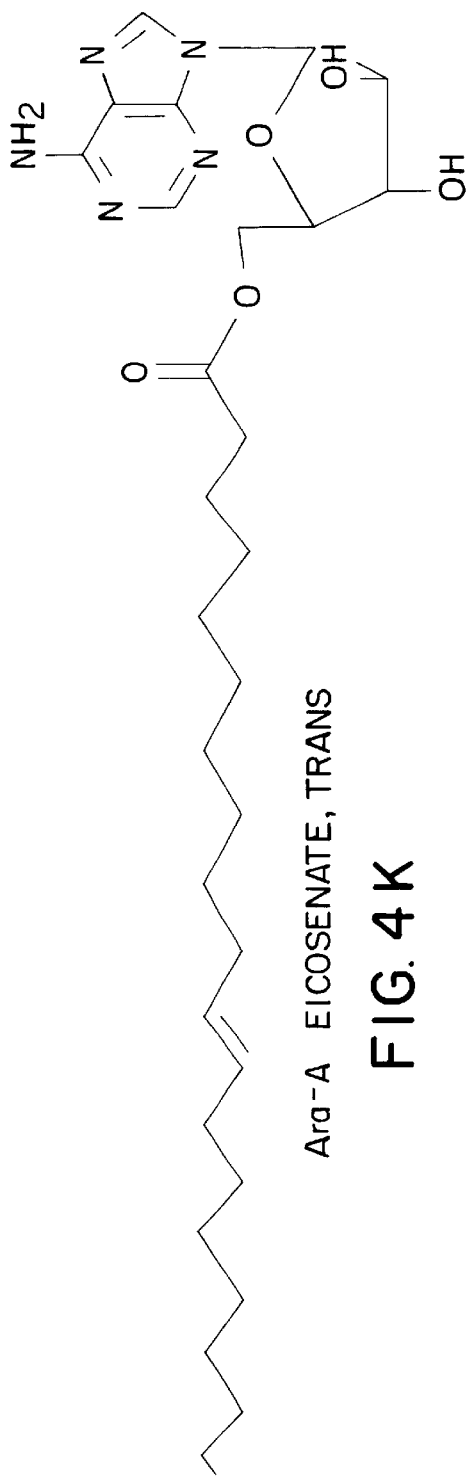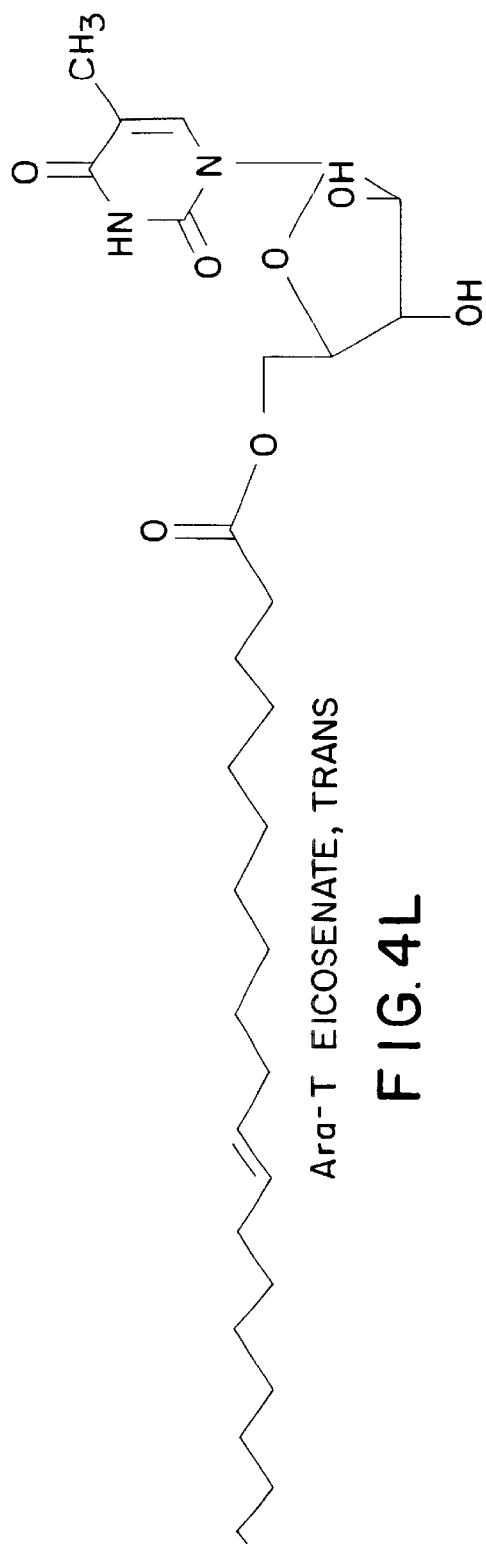

ACV EICOSENATE, TRANS

AZT ELAIDATE

AZT EICOSENATE, cis

AZT EICOSENATE, TRANS

N-6-CH₃-ARA-A ELAIDATE

PCV ELAIDATE

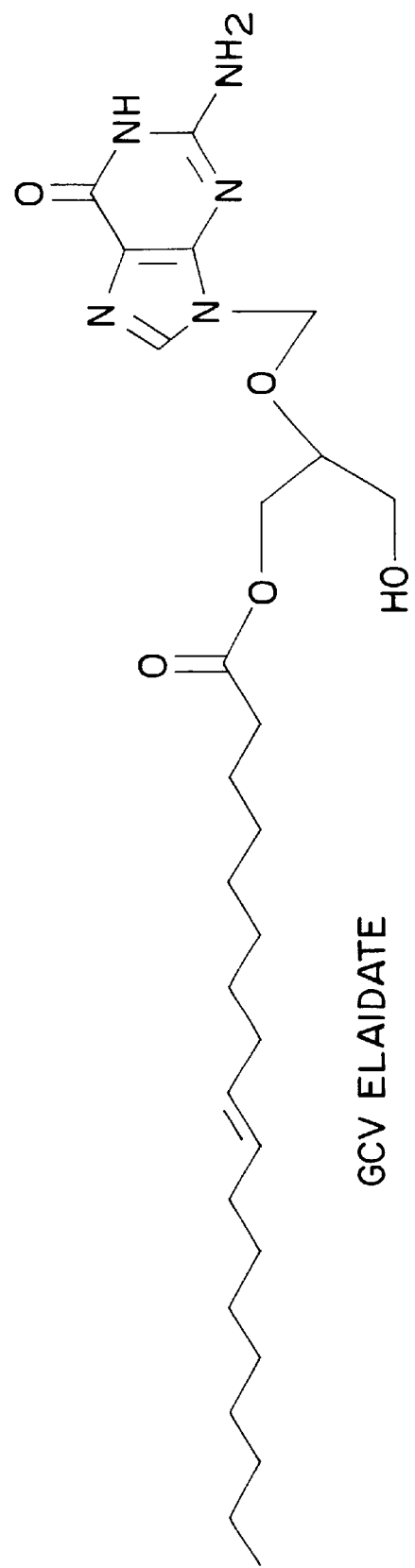
FIG. 4S GCV ELAIDATE

FATTY ACID ESTERS OF NUCLEOSIDE ANALOGS

This application is a 371 of PCT/NO92/00162 filed Sep. 30, 1992.

The present invention relates to a group of new compounds of the general formula I:

Nu-O-Fa wherein O represents an oxygen, Nu is a nucleoside or nucleoside analogue, and Fa is an acyl group of a mono-unsaturated C18 or C20 fatty acid. The invention also concerns anti-viral pharmaceutical and veterinary compositions comprising a compound of formula I alone or in combination with a pharmaceutically acceptable carrier. A further part of this invention is a method for the treatment of a human or animal patient suffering from a viral infection and for reducing the infectious load by administering a compound of formula I.

TECHNICAL BACKGROUND

A large number of serious diseases, such as AIDS, hepatitis B, herpes and gynecological cancer, as a late result of papilloma warts, are caused by viral infections.

Viruses are small infectious agents which are incapable of independent replication and thus are dependent on a host cell to replicate. The genetic material of the virus is either RNA or DNA.

When infecting an organism, the virus attaches to a specific host cell. The virus penetrates the cytoplasmic membrane after attachment and the viral genome is released from the virus particle. The viral genome is usually transported to the cell nucleus where new viral genomes are replicated. New viral protein is synthesized in the cytoplasm and new particles are formed either close to the cytoplasmic or nuclear membrane.

Some viruses have genomic material which is directly (DNA virus) or indirectly (Reverse transcription of RNA, retrovirus) incorporated in the host cell genomes.

Extracellular viruses are neutralized by circulating antibodies and the cellular immune apparatus may attack and remove infected cells. Viruses within the infected cells escape immune surveillance if viral antigens are not exposed on the surface of the cells.

The immune attack on infected organs contributes to disease by a mechanism commonly called virus induced immuno-pathology.

The mechanisms underlying some of the more important viral diseases differ.

When suffering from a HIV infection, the patient's T helper cells are invaded and destroyed. This leads to a immunodeficiency condition, which makes the patient very susceptible even to infections which normally are conquered by the immune system without any harmful effects for the patient.

The Hepatitis B virus invades the liver cells, and the patient may become very ill when the immune system tries to rid the body of these infected cells. If the infection is not conquered by the immune system at an early stage, the result will be chronic hepatitis. The patient will thus be infectious throughout his life. For a group of patients the chronic hepatitis will develop into cirrhosis or cancer of the liver.

In herpes simplex infections, the virus enters the epidermal cells originally. The herpes simplex virus travels up to a nerve center where it lies latent to break out at intervals. Although not life threatening in most cases, a herpes infection is painful and the patient will be infectious every time an outbreak occurs.

In the papilloma virus, notably in the genital tract of women, the viral genome is located in the nucleus of epithelial cells, but not integrated in the cell chromosomes. This is a persistent condition and with some tumor promoting strains an integration finally occurs leading to a malignant development. The viral genome in this case has a decisive initiating effect in the process leading to cancer.

If the immune system manages to rid the body of the virus at an early stage, this leads to a life long immunity. On the other hand, if the virus is too aggressive and avoids the immune apparatus, no immunity is achieved and a continuous infectious state is the result.

As a result of the different mechanisms, the therapeutic strategy would be different for these conditions.

The ultimate goal in the treatment of HIV/AIDS would be to free the patient from the infectious virus. This seems to be remote at the present stage. However, much can be obtained by improving the general condition of the patient. A reduction of the virus load would increase the length of the symptom free period and reduce the infectiousness, which is of utmost importance in regard to the epidemiological situation. All currently used anti-viral agents have toxic side effects, which presently makes a sufficiently aggressive treatment impossible.

It is assumed that there are between 250 and 300 million carriers of hepatitis B world wide. It is known that a great number of these are going to develop hepatomas or liver insufficiencies due to the infections. Promising results in the treatment of the carrier state have been obtained in recent years by induction of an immune response with interferon. Therapies reducing the virus load are important in this regimen as efficient treatment of acute hepatitis B would reduce the number developing into a carrier state. The recently identified hepatitis C virus causes a very great number of cases with hepatitis whereof a large number develop into carriers. Preliminary studies seem to indicate that the carrier state may be broken by similar therapeutic regimens as for hepatitis B. Herpes simplex 1 and 2 frequently infect humans causing a carrier state with recurrencies of local infections. Generalized infections including encephalitis are rare but a catastrophy for the patient. There is a great individual variation in the frequency of local infections. For those patients who are affected either genitally or facially this constitutes a serious health problem physically, mentally and socially. None of the therapeutic regimens developed so far cures the latent infections of cells in the central nervous system. The therapeutic goal is thus to minimize the clinical manifestations of recurrencies both as to symptoms and duration.

The prevalence of genital papilloma virus infections has increased dramatically during the 1980s. It is now established that some genotypes are oncogenic, that is they initiate changes in the cell which after a latency period develop into cancer. Papilloma virus of the genital tract give long standing infections. The factors causing malignant transformation of the lesions are not well understood, but the immune system is assumed to be of importance. It is thought that the lesions showing progression during the months and years are those giving rise to cancer. The genital papillomas called condylomas are at present treated by physical means such as surgical removal, necrotizing means, fluid nitrogen or the like. Genital warts are at the onset benign tumors with altered enzyme patterns affecting among other things the metabolism of nucleoside analogues. Nucleoside prodrugs affect the episomal proliferation of papilloma virus thereby inducing regression of the warts.

Prophylactic vaccination has been very successful in acute infections such as polio, measles, mumps etc., but no effective vaccination has been developed for many of the other serious viral infections.

Even though there have been intensive efforts to produce effective anti-viral chemotherapeutica during the last decades, no satisfactory medical treatment can be offered for most viral diseases today. The efforts have been especially great since the appearance of the HIV and related viral infections, which are spreading throughout the world at an alarming rate, yet the effects obtained with agents such as azidothymidine (AZT) and acyclovir (ACV) in AIDS and herpes can only be characterized as partially successful. These most promising anti-viral agents are thus derivatives of naturally occurring nucleosides, which have been modified either in the base or sugar moiety. They have, however, not had the therapeutic potential hoped for, as they bring forward serious side-effects in some patients or show little or no effect in others. Further, treatment with these agents is extremely expensive. For these reasons only patients suffering from the very serious viral infections such as AIDS receive such treatment. Patients suffering from the less serious, but also very painful viral infections are often left without any treatment to let the infection take its own course.

The untreated patient carries a great infectious load and constitutes a risk to his fellow human beings. If he is treated with an anti-viral agent, the aim is to reduce the infectious load so as to enable the body's immune system to conquer the infection. A further aim is to reduce the contagiousness and thus the number of new patients and carriers.

Thus the need for compounds having a better therapeutic index is obvious.

The need is especially great in chronic or recurrent viral infections with a dangerous acute phase or long term ill effects on health or well being, such as AIDS, hepatitis B and C, infections of the herpes group and papilloma viral infections. Similarly, there is also a need for anti-viral agents usable in the treatment of animals suffering from viral diseases.

Prior Art

In order to improve the effect, there have been developed derivatives of the nuclosides which are either modified in the base or sugar moiety. Especially fatty acid esters of the nucleosides or of analogues of nucleosides have been developed, in order to improve the lipophility and achieve a better membrane passage.

Thus there are known from EP 56265 (Löbering et al.) esters of arabino-furanosyl-thymine (Ara T) with saturated acids having 1–17 C-atoms.

From PCT/WO90/00555 (Hostetler et al.) there are known lipid derivatives linked, epecially through a phosphate group, to the 5'-position of the pentose group of a nucleoside. The purpose of this derivatization was to make the nucleosides more lipophilic so that they could be included into liposomes, which are preferentially taken up by macrophages and monocytes, cells which are found to harbor the HIV virus. It is stated that a targetting effect is thereby achieved.

From EP 393920 there are known unsaturated, preferably polyunsaturated, C16 or higher fatty acid esters or amides of nucleoside or nucleoside analogues. It is stated that the fatty acid portion of these molecules preferably are made up of poly-unsaturated fatty acids, such as γ-linolenic or linoleic acid.

DEFINITION OF THE INVENTION

It has now surprisingly been found that a selected group of fatty acid, esters of anti-viral nucleosides or nucleoside analogues, wherein the fatty acid is a mono-unsaturated C18 or C20 acid gives a much improved effect. Also the compounds according to the present invention seem to be relatively nontoxic as judged by growth experiments with young mice and also have a low cytotoxicity according to observations made in tissue culture experiments.

Although it is known that both nucleosides and nucleoside analogues, by themselves, and also some unsaturated fatty acids, by themselves, exhibit anti-viral effects, the magnitude of the effects achieved with the compounds according to this invention indicates that this is not an additive, but rather a synergistic activity which is special for the compounds of formula I.

The mechanism behind these effects is at present not known, but they are of an order of magnitude better than the closest related compounds of the prior art. Thus it is not considered likely that they arise only due to a membrane effect or targetting effect.

Further it is also clear, as will appear from the biological examples included herein, that effects are achieved with these compounds in systems where no effects may be achieved with the mother nucleoside compound.

The compounds of this invention can be characterized by the general formula I:

wherein O is an oxygen, Nu is a nucleoside or nucleoside analogue and Fa is an acyl group of a mono-unsaturated C18 or C20 fatty acid.

Nucleosides are molecules comprising a heterocyclic base, such as cytosine, uracil, adenine or guanine, linked to a ribose unit. In nucleoside analogues, either the base or the ribose unit has been modified. For example, the ribose unit may be replaced by another sugar unit or by a noncyclic chain.

The fatty acid is esterified with a hydroxyl group in the 5-position of the sugar moiety of the nucleoside or with a hydroxyl group on the non-cyclic group of the nucleoside analogue.

The nucleoside or nucleoside analogues which may be chosen as Nu in the compounds of formula I may preferably be represented by the formula II:

 (II)

wherein S is either a mono-saccharide-derivative selected from: 1-β-D-arabinofuranose or 2,3-di-deoxy-3-azido-1-β-D-ribofuranose, or selected from the group of 2-hydroxy-ethoxy-methyl, 4-hydroxy-3-(hydroxymethyl)-butyl, 2-hydroxy-1-(hydroxy-methyl)-ethoxy-methyl or 2,3-dihydroxy-propoxy; and B is a nitrogen base selected from adenine, guanine, cytosine, uracil, thymine or a thymine derivative of the following formula:

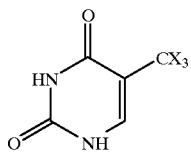

Wherein X is deuterium or fluorine.

Examples of these nucleosides or nucleoside analogues are:

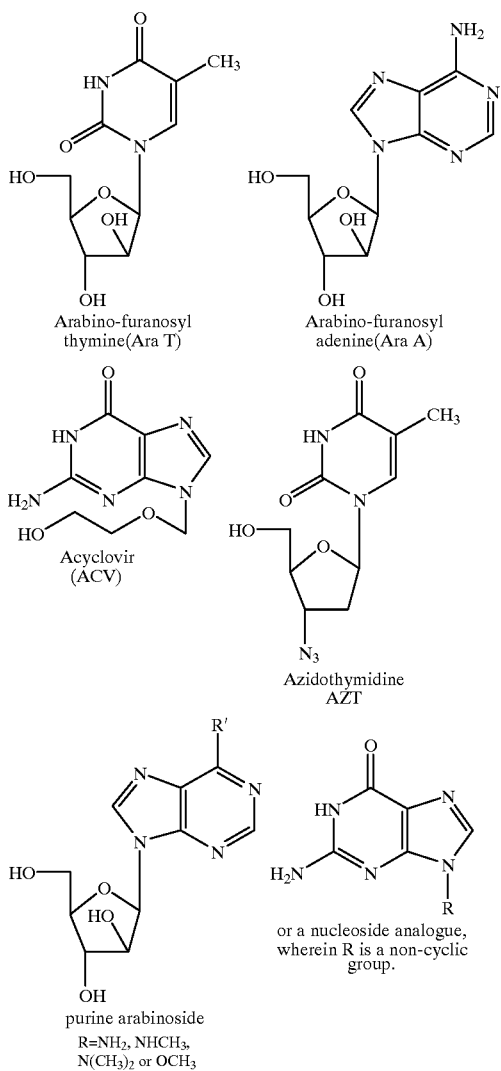

Examples of the group R in different nucleoside analogues appear below:

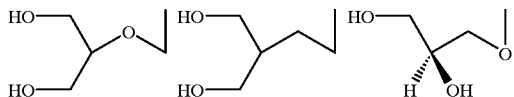

There exist several systems for denomination of the position of double bonds in fatty acids. In the present application the ω-system is used, wherein the position of the double bond in the unsaturated fatty acids is counted from the terminal methyl group. Eicosenic acid (C20:1 ω-9), for example, has 20 carbon atoms in the chain, and the double bond is found between carbon atom 9 and 10 counting from the end of the chain.

The fatty acids which are reacted with the nucleosides or nucleoside analogues to form the esters according to this invention with the pronounced activity are the ω-9 C18 or C20 monounsaturated fatty acids. Further, even though the effect observed differs somewhat between acids of the same chain length when the double bond is in cis or trans configuration, both show a strong activity. Also the position of the double bond is of importance, as it appears that especially the esters with a C18 or C20 fatty acid having the unsaturation in ω-9 position will have the surprisingly elevated activity.

The C18 or C20 ω-9 fatty acids, which when bound to the nucleosides give the surprisingly elevated effect, are the following: oleic acid (C18:1, ω-9, cis), elaidic acid (C18:1, ω-9, trans) eicosenic acid, (c20:1, ω-9, cis) and (C20:1, ω-9, trans)

Preferred representatives of the compounds according to this invention are listed below.: Ara A-oleic acid, Ara A-elaidic acid, Ara A-eicosenic acid, cis, Ara A-eicosenic acid, trans, Ara T-oleic acid, Ara T-elaidic acid, Ara T-eicosenic acid, cis, Ara T-eicosenic acid, trans, ACV-oleic acid, ACV-elaidic acid, ACV-eicosenic acid, cis, ACV-eicosenic acid, trans, AZT-oleic acid, AZT-elaidic acid, AZT-eicosenic acid, cis, AZT-eicosenic acid, trans. Their formulas will appear from FIG. 4.

The compounds according to this invention exhibit antiviral effects, and the present invention thus includes pharmaceutical or veterinary compositions comprising at least one compound of formula I alone or in combination with a pharmaceutically acceptable carrier or excipient. In the remainder of the text and in the claims, a pharmaceutical composition will be used for compositions usable in the treatment of both human and animal patients.

Further, it appears that certain of the monounsaturated fatty acid nucleosides or nucleoside analogues will be especially suitable for the treatment of certain viral infections. Thus it appears that the fatty acid derivatives of AZT are especially useful for the treatment of AIDS.

Similarly, it appears that the fatty acid derivatives of Ara T and Ara A are especially suitable for the treatment of hepatitis B. It appears also that the Ara T esters will be efficient in agents suitable for treatment of papilloma viral infections.

Further, it appears that the fatty acid esters according to this invention of ACV are especially suitable for the treatment of herpes infections.

As mentioned, the production of the necessary immune response in order to conquer a viral infection, such as hepatitis, can be induced in some cases by the co-administration of interferon.

Depending on which viral infection is to be treated and at what stage the infection is, or if the patient is a human being or an animal, both a systemic and a local administration of the compounds can take place.

For local administration, the compounds can be formulated as known in the art for administration to the skin or mucosa in any suitable form.

When administered topically the compounds of formula I may be formulated as an ointment, cream, gel, tincture, spray, lotion or the like containing the compounds of formula I in admixture with inert, solid or liquid carriers which are usual in topical preparations. It is especially suitable to use a formulation which protects the active ingredient against oxidation or degradation.

The pharmaceutical preparations comprising the compounds of formula I may also be administered systemically, either enterally or parenterally.

When administered enterally, the compounds of formula I may be formulated e.g. as soft or hard gelatine capsules, tablets, granules, grains or powders, dragees, syrups, suspensions or solutions.

When administered parenterally, preparations of the compounds of formula I as injection or infusion solutions, suspensions or emulsions are suitable.

The preparations can contain inert or pharmacodynamically active additives. Tablets or granulates e.g. can contain a series of binding agents, filler materials, carrier substances or diluents. Liquid preparations may be present, for example, in the form of a sterile solution. Capsules can contain a filler material or thickening agent in addition to the active ingredient. Furthermore, flavor-improving additives as well as the substances usually used as preserving, stabilizing, moisture-retaining and emulsifying agents, salts for varying the osmotic pressure, buffers and other additives may also be present.

The dosages in which the preparations according to this invention are administered will vary according to the mode of use and the route of use, as well as to the requirements of the patient. In general a daily dosage for a systemic therapy for an adult average patient will be about 0.1–100 mg/kg body weight/day, preferably 1–20 mg/kg/day. For topical administration, the suitable ointment can contain from 0.1–10% by weight of the pharmaceutical formulation, especially 0.5–5% by weight.

If desired, the pharmaceutical preparation of the compound of formula I can contain an antioxidant, e.g. tocopherol, N-methyl-tocopheramine, butylated hydroxyanisole, ascorbic acid or butylated hydroxytoluene.

The invention further discloses a method for the treatment of viral infections, which comprises administering at least one compound of formula I to a human or animal patient in need of such treatment.

Further, the invention also comprises a method for the treatment of a patient in need of such treatment with a combination of a compound of formula I and an interferon.

Biological Effects

DESCRIPTION OF FIGURES

FIG. 1B shows a comparison of two of the compounds according to this invention with the mother nucleoside at two different concentrations.

FIG. 3 shows a comparison of the rate of survival in young mice infected with HSV 2 after administration of ACV and ACV elaidate.

A. In Vitro Experiments

The Plaque Method: Tissue Culture of Virus

A virus preparation of HSV 2 (3rd passage of a clinical isolate) is diluted to $3\times10^3$ pfu/well, and thereafter inoculated on cells and incubated for 1 hour in a tissue culture of vero cells. At that time the virus is incorporated into the cells.

These cells are then cultivated for 24 hours with an anti-viral agent. Thereafter they are placed under freezing conditions, which lead to the disruption of the cells and free virus appear under the melting process. Dilutions of either 1/100 or 1/10000 are prepared and added to fresh tissue cultures. Incubation for 1 hour leads to incorporation of virus in the cells. Carboxymethylcellulose (CMC) is added in order to prohibit the migration of virus between the cells through the medium. Spread of virus by cell contact is still effective in causing the formation of plaques.

One plaque will represent one infectious virus. Thus the counting of plaques gives a precise quantitation of the number of infectious virus.

1.1 Acyclovir esters

Figure 1A:
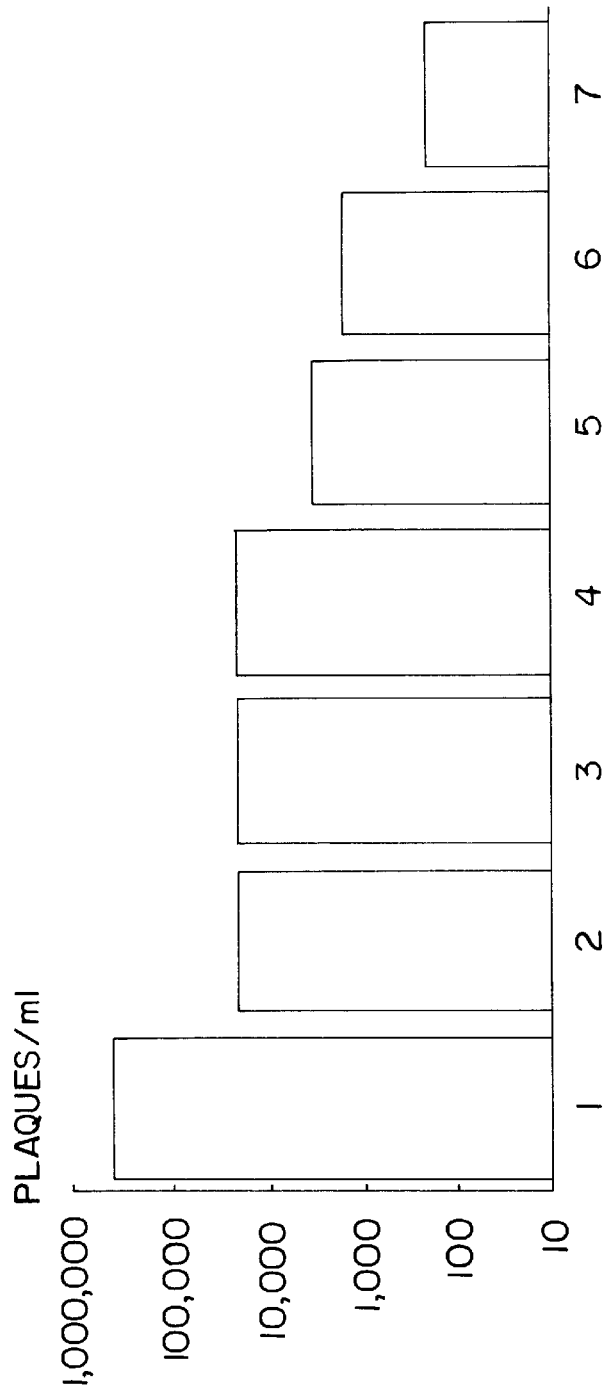
FIG. 1A shows the inhibitory effect of fatty acid esters of ACV; compounds according to the present invention are compared with a prior art compound (ACV linolenate, see EP-A-393920) and a C22 monounsaturated ($\omega$-9) ester, (ACV erucate).

Different antiviral agents according to this invention and the prior art as disclosed in EP 393920, and also a comparable longer chain monounsaturated fatty acid ester were added to the tissue culture dissolved in dimethylsulphoxide (DMSO) in a concentration of 0.94 $\mu$mol/l. This concentration is below the effective incubatory concentration of acyclovir in the Herpes Simplex 2 strain used. The results are shown in FIG. 1A. As will appear from FIG. 1A, the nucleoside fatty acid esters according to this invention have even at this concentration an inhibitory effect on virus by magnitudes better than the mother compound acyclovir. Further, FIG. 1A shows the enhanced inhibitory effect, when compared to compounds according to the prior art represented by ACV $\gamma$-linolenate (C18:3 $\omega$-3) and also when compared to a longer chain monounsaturated fatty acid nucleoside ester, ACV erucate (C22:1 $\omega$-9), having the unsaturation at the same position of the chain. The inhibitory effect achieved with the three representatives of the present compounds are close to 100%.

The effect of increasing concentrations is shown in FIG. 1B. In a test done with a HSV 2 strain relatively resistent to ACV, the test compounds, ACV, ACV-oleate and ACV-elaidate, were added at 0.9 $\mu$mol/l or 2.2 $\mu$mol/l. As will appear, the inhibitory effect of the compounds according to this invention is strongly enhanced at the higher concentration, whereas the effect of the mother nucleoside, ACV, remains at the same level.

1.2. Ara T esters

Figure 2:
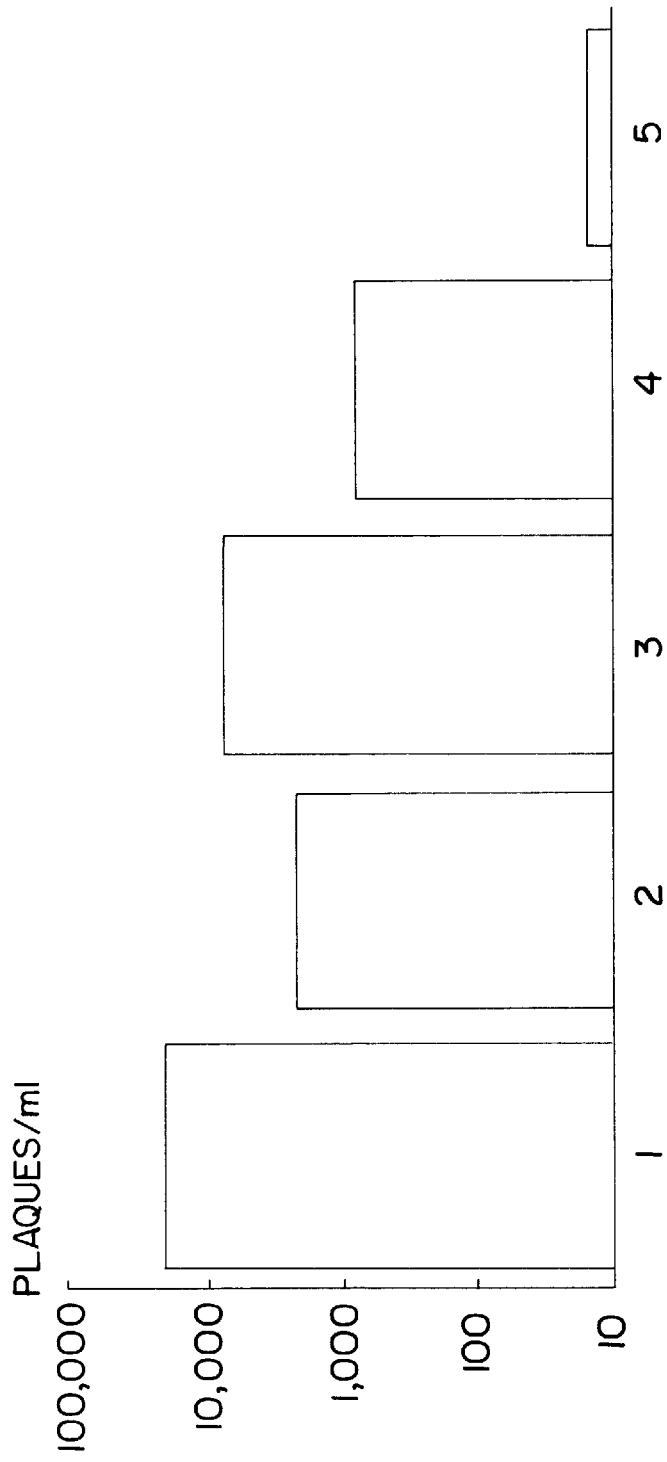
FIG. 2 shows the inhibitory effect achieved with Ara T esters; a compound according to the present invention is compared with a prior art saturated Ara T ester (Ara T palmitate, see EP-56265), the mother nucleoside and a monounsaturated C11 Ara T ester (Ara T undecenate).
Figure 4E:
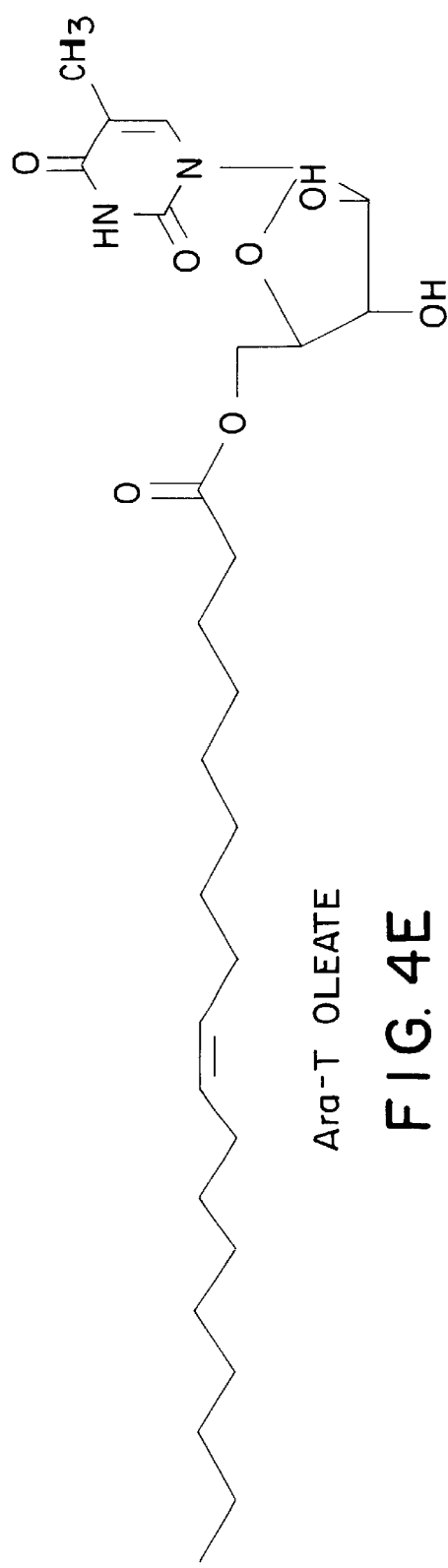
FIGS. 4A through 4S show the full structure of the most preferred compounds according to this invention.
Figure 4F:
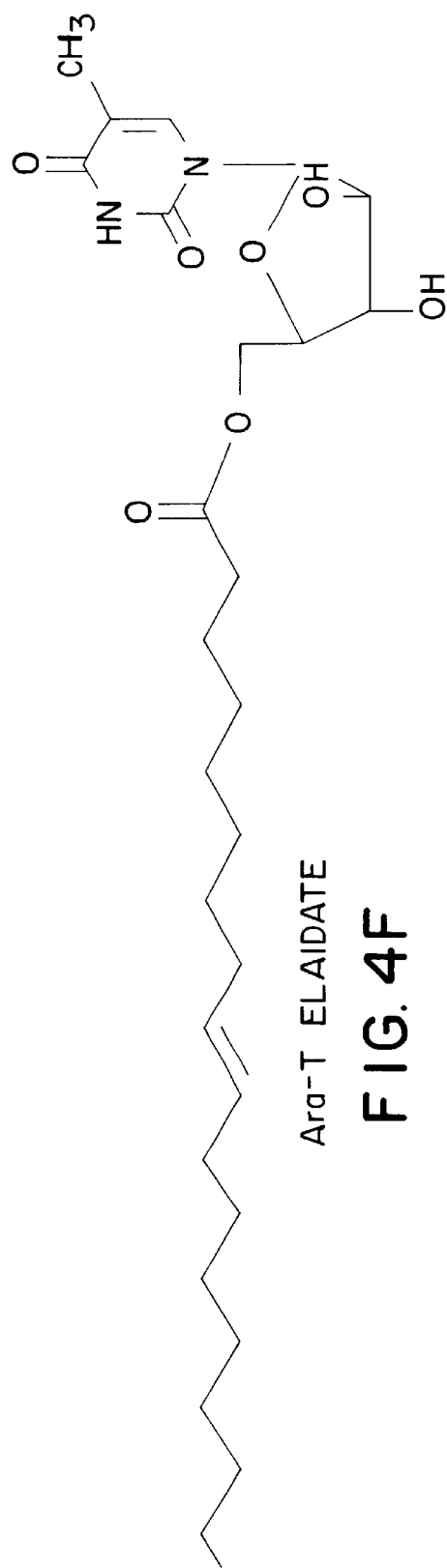
Figure 4I:
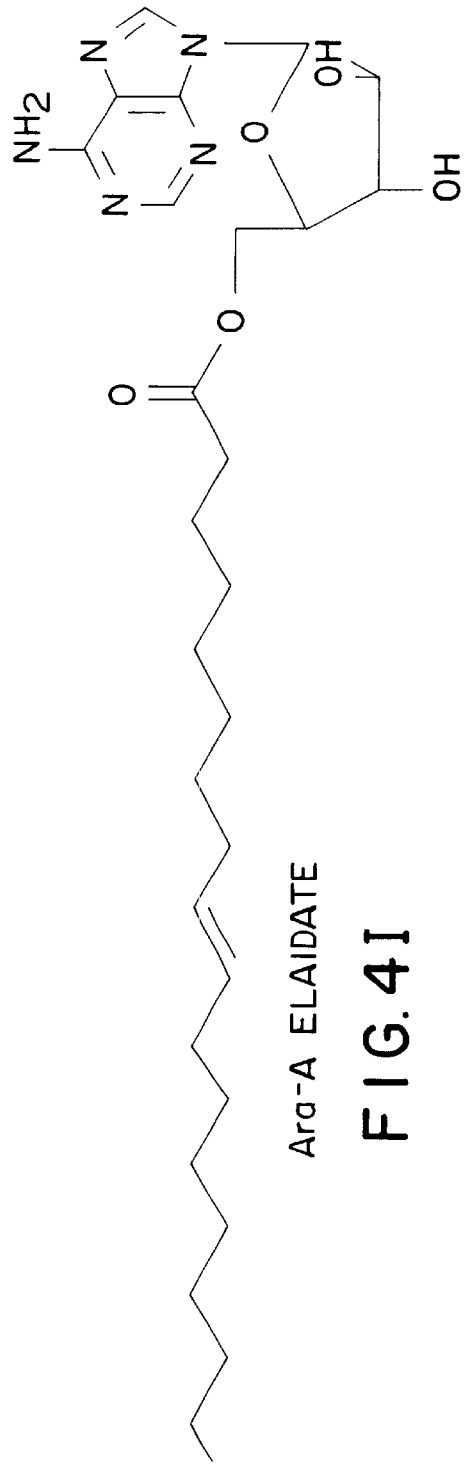
Figure 4J:
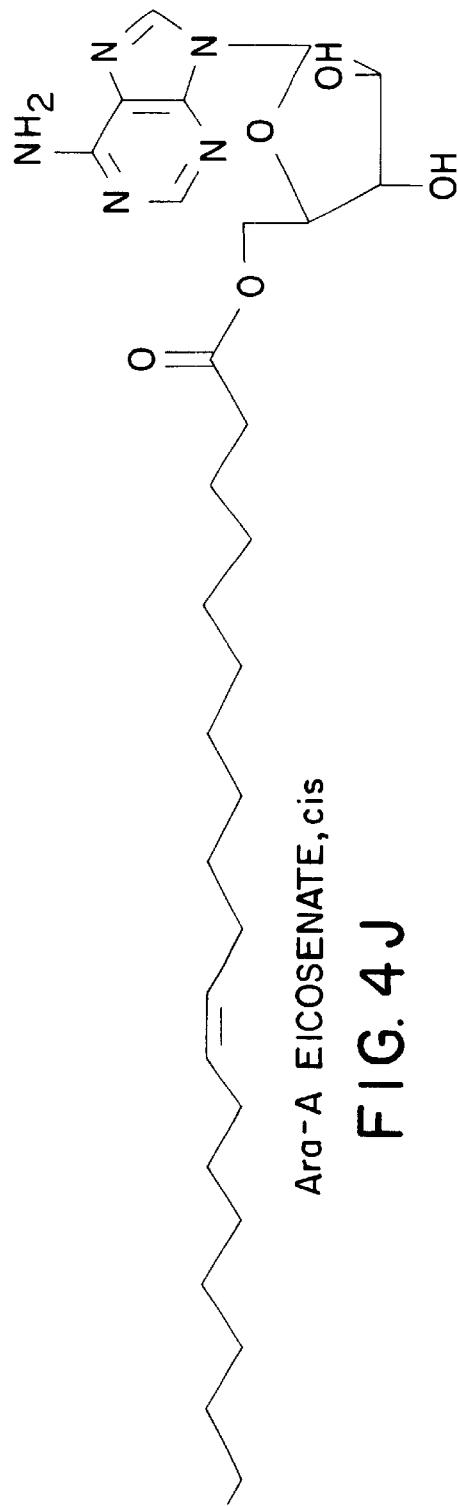
Figure 4M:
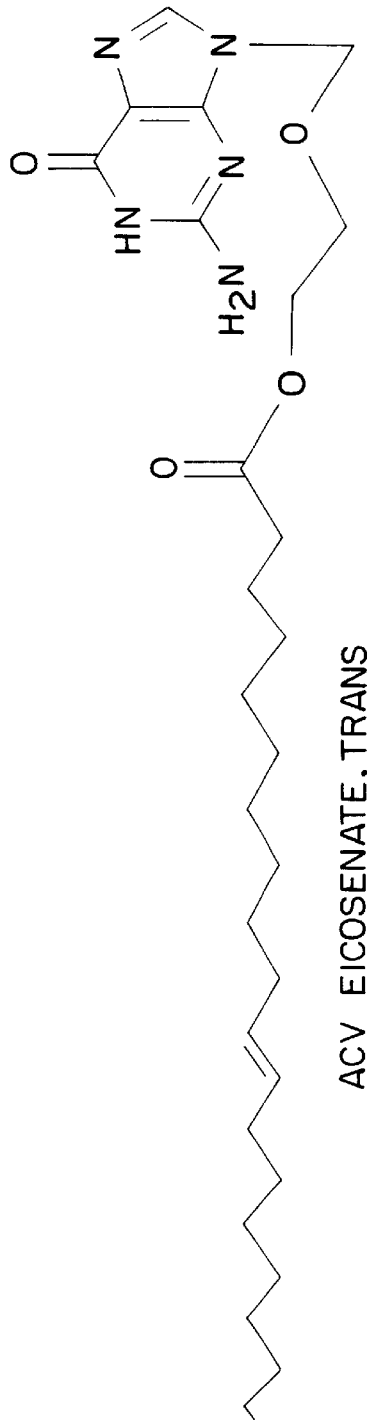
Figure 4N:
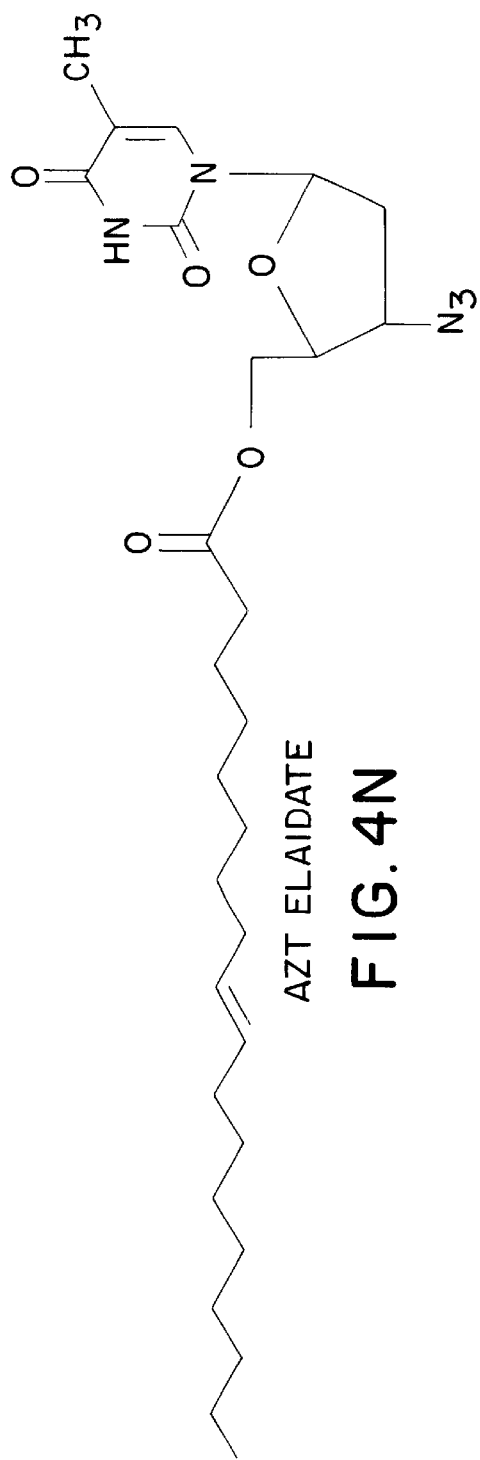
Figure 4O:
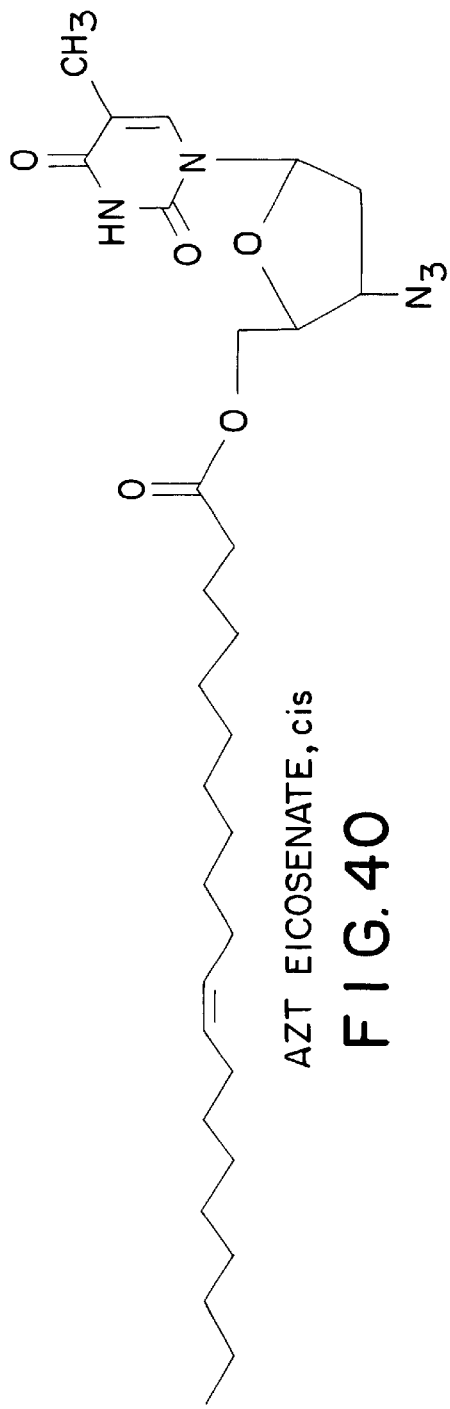
Figure 4P:
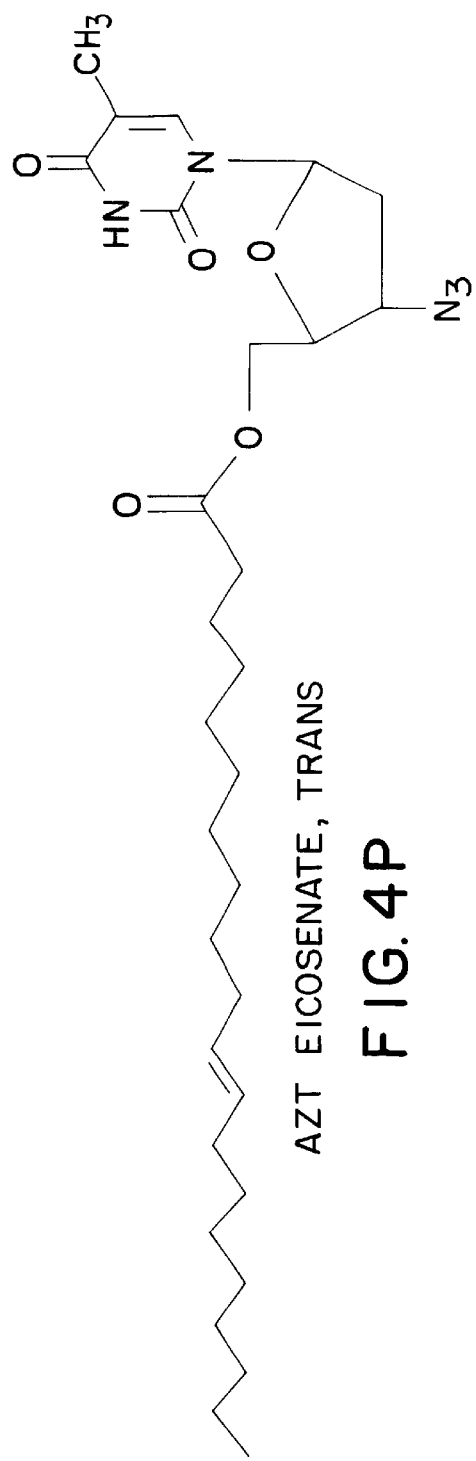
Figure 4Q:
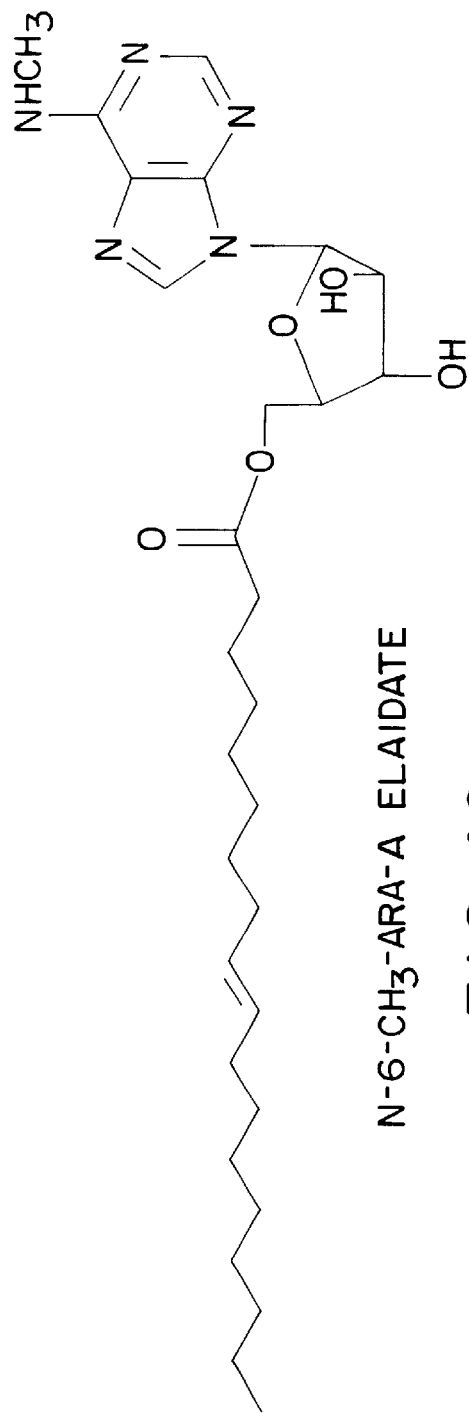
Figure 4R:
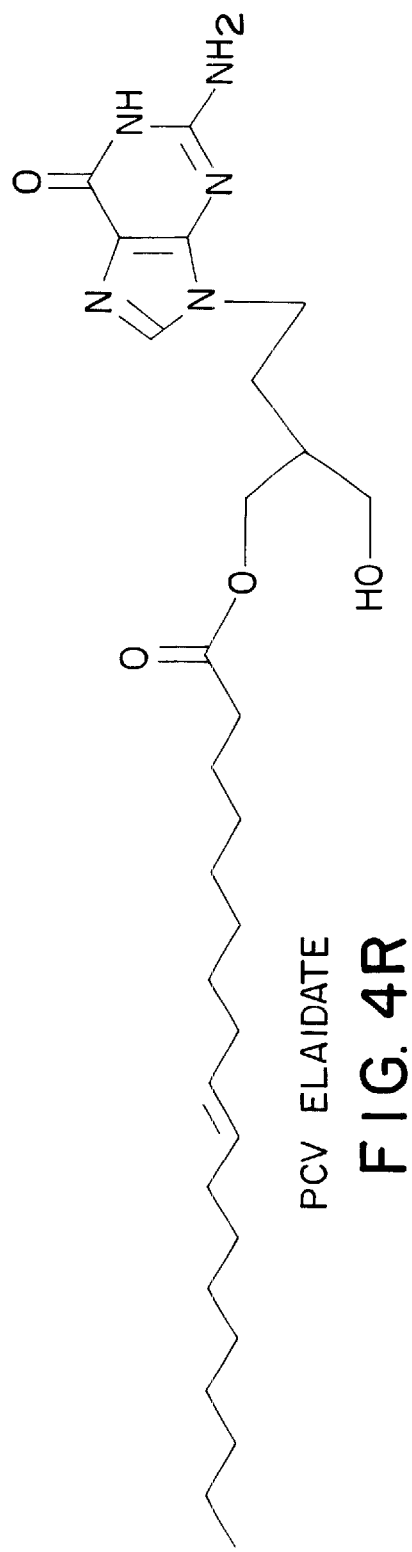

Corresponding experiments were conducted with Ara T, Ara T-oleate, one saturated fatty acid ester representing prior art, Ara T-palmitate (C16:0) and Ara T-undecenate (C11:1, $\omega$-1), representing a shorter length, monounsaturated fatty acid ester. The anti-viral agents were added at a concentration of 3.9 $\mu$mol/l. The results will appear from FIG. 2.

As previously noted for the ACV esters, the Ara T ester according to this invention, Ara T oleate, has a strikingly improved inhibitory activity. The inhibition achieved in this test is 100%.

B. In Vivo Results Achieved—Reduced Mortality Herpes Simplex Virus 2

The in vivo experiments were done using 3–4 weeks old female NMRI mice. This strain of mice is sensitive to the human herpes virus, up to an age of about 6 weeks, where after they become relatively resistant. Mice below this critical age were used, having a weight of 13–17 grams.

Herpes virus 2 which were third passage isolates were inoculated on the left ear lobe by a standarized procedure. After 3 days a local infection was established. Under these conditions, the HSV 2 was highly neurotropic and 95% of the animals developed fatal encephalitis, usually after 7–9 days. Thus HSV 2 is especially suitable as a system for evaluation of the therapeutic efficiency by counting the number of cases of encephalitis.

The administration of the test compounds were done at a very low concentration in order better to observe differences in effect. The animals received approximately 12 mg/kg body weight/day through the drinking water. The compounds were added to the drinking water formulated as micelles with deoxycholate. The final concentration was 0.22 mmol/l.

Both the control group and the groups receiving the test compounds included 10 animals in each group. The test compounds were ACV-elaidate and ACV in comparison with the control. Treatment was started on day 3 from inoculation. At that time the infection is well established in the central nerve system. The mortality of the animals was plotted and the results are shown in FIG. 3.

This test system represents extremely severe conditions. As appears from FIG. 3, all the animals in the control group died from the infection. The mother nucleoside acyclovir has no therapeutic effect at this concentration when treatment is started after the infection is well established, on day 3 after infection.

As will be appearant the survival rate is improved from 0 to 40% for the animals receiving ACV-elaidate. After 21 days the animals in this group looked ruffled, but showed no signs of encephalitis.

Preparation

The compounds of formula I may generally be prepared according to the following reaction equotation:

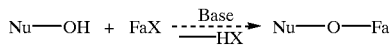

wherein Nu, O and Fa are as defined above, and X may be Cl, Br, O—CO—R', wherein R' is Fa, $CH_3$, $CH_2CH_3$, or $CF_3$.

Thus the reaction proceeds by acylation of the nucleoside or nucleoside analogue. This is accomplished by the use of suitable reactive derivatives of the fatty acids, especially acid halides or acid anhydrides. When an acid halide such as an acid chloride is used, a tertiary amine catalyst, such as triethylamine, N,N-dimethylaniline, pyridine or N,N-dimethylaminopyridine is added to the reaction mixture to bind the liberated hydrohalic acid. The reactions are preferably carried out in an unreactive solvent such as N,N-dimethylformamide or a halogenated hydrocarbon, such as dichloromethane. If desired, any of the above mentioned tertiary amine catalysts may be used as solvent, taking care that a suitable excess is present. The reaction temperature can be varied between 0° C. and 40° C., but will preferably be kept between 5° C. and 25° C. After a period of 24 to 60 hours, the reaction will be essentially completed. The progress of the reaction can be followed using thin layer chromatography (TLC) and appropriate solvent systems. When the reaction is completed as determined by TLC, the product is extracted with an organic solvent and purified by chromatography and/or recrystallization from an appropriate solvent system. If more than one hydroxyl group or also amino groups are present in the nucleoside or nucleoside analogue, a mixture of acylated compounds may be produced. The individual mono- or polyacylated compounds may be separated by, for instance, chromatography.

This will further be examplified by the following working examples:

EXAMPLE 1

5'-O-Hexadecanoyl-1-β-D-Arabinofuranosyl-Thymine

To a solution of 1-β-D-Arabinofuranosyl-Thymine (ARA-T) (0.5 g, 1.94×10$^{-3}$ mol) in 20 ml anhydrous pyridine was added 3 ml of a stock solution of palmitoylchloride (0.58 g, 2.13×10$^{-3}$ mol) in 5.5 ml dichloromethane. The reaction mixture was stirred under nitrogen at room temperature for 12 hours when thin layer chromatography showed partial conversion. The remaining palmitoylchloride solution was added and the resulting mixture was stirred for 24 hours. The reaction mixture was evaporated to dryness and the residue was partitioned between 50 ml chloroform and 50 ml water. Centrifugation of the resulting emulsion afforded a semisolid that was recrystallized from ethanol/heptane 1:1 to give 0.7 g (72%) of the title compound as a white solid.

$^1$H NMR (DMSO-$d_6$, 300 MHz)δ:11.25(1H,s,N—H), 7.32(1H,s,H-6), 6.05(1H,d,H-1'), 5.65(1H,d,OH-2'), 5.58 (1H,d,OH-3'), 4.50(1H,m,H-5'$_1$), 4.15(1H,m,H-5'$_2$), 4.02 (1H, m, H-2'), 3.92(1H,m,H-3'), 3.88(1H,m,H4'), 2.31(2H, t,$CH_2$—COO), 1.75(3H,s,$CH_3$-5), 1.55(2H,m,$CH_2$—C—COO), 1.20(24H,m,$CH_2$), 0.85(3H,t,$CH_3$—$CH_2$).

$^{13}$C NMR (DMSO-$d_6$, 75 MHz)δ: 172.81(COO), 163.78 (CO-4), 150.37(CO-2), 137.88(C-6), 107.21(C-5), 85.29(C-1'), 81.74(C4'), 76.06(C-3'), 74.65(C-2'), 63.23(C-5'), 33.41, 31.26, 28.97, 28.82, 28.66, 28.33, 24.44, 22.05($CH_2$), 13.89 ($CH_3$—$CH_2$), 12.15($CH_3$-5).

EXAMPLE 2

5'-O-(cis-9"-Hexadecenoyl)-1-β-Arabinofuranosyl-Thymine

To a solution of cis-9-Hexadecenoic acid (4.0 g, 15.72× 10$^{-3}$ mol) in 40 ml anhydrous benzene was added oxalylchloride (1.5 ml, 17.72×10$^{-3}$ mol) and the mixture was stirred under nitrogen at 35° C. for 3 hours. The solvent and exess reagent was removed at high vacuum, and the residue was dilluted with 10 ml dichloromethane to prepare a stock solution of cis-9-Hexadecenoylchloride. To a solution of ARA-T (1.0 g, 3.87×10$^{-3}$ mol) in 20 ml anhydrous pyridine and 10 ml N,N-dimethylformamide was added 2 ml of the stock solution and the reaction mixture was stirred under nitrogen at room temperature. A further volume of 4 ml stock solution was added in 1 ml portions at approx 8 hours intervals. After a total of 60 hours reaction time, the solvents were removed at high vacuum and the residue was dilluted with 50 ml water and 50 ml chloroform. Centrifugation of the resulting emulsion afforded a semisolid mass that was recrystallized from ethanol/heptane 1:1 to give 1.15 g (60%) of the title compound as a white solid.

$^1$H NMR (DMSO-$d_6$, 300 MHz)δ: 11.25(1H,s,N—H), 7.32(1H,s,H-6), 6.05(1H,d,H-1'), 5.65(1H,d,OH-2'), 5.55 (1H,d,OH-3'), 5.3(2H,m,—CH═CH—), 4.45(1H,m,H-5'$_1$), 4.15(1H,m,H-5'$_2$), 3.98(1H,n,H-2'), 3.95(1H,m,H-3'), 3.90 (1H,m,H-4'), 2.35(2H,t,$Ch_2$—COO), 1.98(4H,m,═CH—$CH_2$—), 1.75(1H,t,$CH_3$-5), 1.52(2H,m,$CH_2$—C—COO), 1.20(16H,m,$CH_2$), 0.85(3H,t,$CH_3$—$CH_2$).

$^{13}$C NMR (DMSO-$d_6$, 75 MHz)δ: 172.31(COO), 163.31 (CO-4), 149.90(CO-2), 137.89(C-6), 129.13 and 129.03(—CH═CH—), 106.74(C-5), 84.83(C-1'), 81.26(C-4'), 75.59 (C-3'), 74.16(C-2'), 62.76(C-5'), 32.98, 30.62. 28.57, 28.50, 28.02, 27.91, 27.84, 27.76, 26.07, 26.03, 23.95, 21.56($CH_2$), 13.39($CH_3$—$CH_2$—), 11.68($CH_3$-5).

EXAMPLE 3

5'-O-(cis-6"-Octadecenoyl)-1-β-D-Arabinofuranosyl-Thymine

To a solution of ARA-T (1.0 g, $3.87 \times 10^{-3}$ mol) in 20 ml anhydrous pyridine and 10 ml N,N-dimethylformamide was added 2 ml of a stock solution of cis-6-Octadecenoylchloride (2.1 g, $6.98 \times 10^{-3}$ mol) in 6 ml dichloromethane, and the reaction mixture was stirred under nitrogen at room temperature. The remaining stock solution was added in 2 ml portions at approx. 12 hours intervals. After a total of 60 hours reaction time, the solvents were evaporated at high vacuum and the residue was dilluted with 65 ml chloroform and 65 ml water. The resulting emulsion was centrifugated and the organic phase was treated with brine, concentrated and the residue was recrystallized to give 1.1 g (55%) of the title compound as a white solid.

$^1$H NMR (DMSO-$d_6$, 300 MHz)δ: 11.28(1H,s,N—H), 7.35(1H,s,H-6), 6.05(1H,d,H-1'), 5.65(1H,d,OH-2'), 5.55 (1H,d,OH-3'), 5.28(2H,m,CH=CH), 4.45(1H,m,H-5'$_1$), 4.15(1H,m,H-5'$_2$), 3.98(1H,m,H-2'), 3.95(1H,m,H-3'), 3.90 (1H,m,H-4'), 2.35(2H,t,$Ch_2$—COO), 1.97(4H,m,$CH_2$—CH=), 1.75(3H,s,$CH_3$-5), 1.52(2H,m,$CH_2$—C—COO), 1.25(20H,m,$CH_2$), 0.85(3H,t,$CH_3$—$CH_2$).

$^{13}$C NMR (DMSO-$d_6$, 75 MHz)δ: 172.73(COO), 163.81 (CO4), 150.40(CO-2), 137.88(C-6), 129.88 and 129.10 (CH=CH), 107.24(C-5), 85.34(C-1'), 81.76(C4'), 76.10(C-3'), 74.66(C-2'), 63.28(C-5'), 33.29, 31.28, 28.99, 28.84, 28.69, 28.57, 28.43, 26.54, 26.29, 24.07, 22.07($CH_2$), 13.89 ($CH_3$—$CH_2$), 12.16($CH_3$-5).

EXAMPLE 4

5'-O-(cis-9"-Octadecenoyl)-1-β-D-Arabinofuranosyl-Thymine

To a solution of ARA-T (1.0 g, $3.87 \times 10^{-3}$ mol) in 20 ml anhydrous pyridine and 10 ml N,N-dimethylformamide was added 2 ml of a stock solution of cis-9-Octadecenoylchloride (2.1 g, $6.98 \times 10^{-3}$ mol) in 6 ml dichloromethane, and the reaction mixture was stirred under nitrogen at room temperature. The remaining stock solution was added in 2 ml portions at approx. 12 hours intervals. After a total of 60 hours reaction time, the solvents were evaporated at high vacuum and the residue was dilluted with 65 ml chloroform and 65 ml water. The resulting emulsion was centrifugated and the organic phase was treated with brine, concentrated and the residue was recrystallized to give 1.2 g (60%) of the title compound as a white solid.

$^1$H NMR (DMSO-$d_6$, 300 MHz)δ: 11.28(1H,s,N—H), 7.35(1H,s,H-6), 6.05(1H,d,H-1'), 5.65(1H,d,OH-2'), 5.55 (1H,d,OH-3'), 5.28(2H,m,CH=CH), 4.45(1H,m,H-5'$_1$), 4.15(1H,m,H-5'$_2$), 3.98(1H,m,H-2'), 3.95(1H,m,H-3'), 3.90 (1H,m,H-4'), 2.35(2H,t,$CH_2$—COO), 1.97(4H,m,$CH_2$—CH=), 1.75(3H,s,$CH_3$-5), 1.52(2H,m,$CH_2$—C—COO), 1.25(20H,m,$CH_2$), 0.85(3H,t,$CH_3$—$CH_2$).

$^{13}$C NMR (DMSO-$d_6$, 75 MHz)δ: 172.75(COO), 163.80 (CO-4), 150.39(CO-2), 137.88(C-6), 129.58 and 129.49 (CH=CH), 107.21(C-5), 85.36(C-1'), 81.79(C-4'), 76.11 (C-3'), 74.67(C-2), 63.26(C-5'), 33.42, 31.27, 29.08, 29.02, 28.84, 28.68, 28.55, 28.43, 28.37, 26.54, 24.44, 22.07($CH_2$), 13.86($CH_3$—$CH_2$), 12.15($CH_3$-5).

EXAMPLE 5

5'-O-(trans-9"-Octadecenoyl)-1-β-D-Arabinofuranosyl-Thymine

To a solution of ARA-T (1.0 g, $3.87 \times 10^{-3}$ mol) in 20 ml anhydrous pyridine and 10 ml N,N-dimethylformamide was added 2 ml of a stock solution of trans-9-Octadecenoylchloride (2.1 g, $6.98 \times 10^{-3}$ mol) in 6 ml dichloromethane, and the reaction mixture was stirred under nitrogen at room temperature. The remaining stock solution was added in 2 ml portions at approx. 12 hours intervals. After a total of 60 hours reaction time the solvents were evaporated at high vacuum and the residue was dilluted with 65 ml chloroform and 65 ml water. The usual work up and recrystallization gave 1.30 g (65%) of the title compound id as a white solid.

$^1$H NMR (DMSO-$d_6$, 300 MHz)δ: 11.25(1H,s,N—H), 7.35(1H,s,H-6), 6.05(1H,d,H-1'), 5.65(1H,d,OH-2'), 5.55 (1H,d,OH-3'), 5.35(2H,m,CH=CH), 4.45(1H,m,H-5'$_1$), 4.15(1H,m,H-5'$_2$), 4.0(1H,m,H-2'), 3.95(1H,m,H-3'), 3.90 (1H,m,H-4'), 2.35(2H,t,$CH_2$—COO), 1.93(4H,m,$CH_2$—CH=), 1.75(3H,s,$CH_3$-5), 1.51(2H,m,$CH_2$—C—COO), 1.25(20H,m,$Ch_2$), 0.85(3H,t,$CH_3$—$CH_2$).

$^{13}$C NMR (DMSO-$d_6$, 75 MHz)δ: 172.77(COO), 163.88 (CO-4), 150.45(CO-2), 137.98(C-6), 130.03, and 129.97 (CH=CH), 107.24(C-5), 85.44(C-1'), 81.89(C4'), 76.17(C-3'), 74.69(C-2'), 63.34(C-5'), 33.48, 31.99, 31.35, 29.06. 29.00, 28.91, 28.78, 28.61, 28.56, 28.44, 28.40, 24.50 and 22.15($CH_2$), 13.90($CH_3$—$CH_2$), 12.20($CH_3$-5).

EXAMPLE 6

5'-O-(cis-11"-Octadecenoyl)1-β-D-Arabinofuranosyl-Thymine

To a solution of ARA-T (1.0 g, $3.87 \times 10^{-3}$ mol) in 20 ml anhydrous pyridine and 10 ml N,N-dimethylformamide was added 2 ml of a stock solution of cis-11-Octadecenoylchloride (2.1 g, $6.98 \times 10^{-3}$ mol) in 6 ml dichloromethane, and the reaction mixture was stirred under nitrogen at room temperature. The reaction was completed in the usual manner, and the crude product was purified on a column of silica gel with 5% methanol in chloroform as the eluent system. Homogeneous fractions were evaporated to give 1.2 g (55%) of the title compound as a white solid.

$^1$H NMR (DMSO-$d_6$, 300 MHz)δ: 11.25(1H,s,N—H), 7.35(1H,s,H-6), 6.05(1H,d,H-1'), 5.65(1H,d,OH-2'), 5.55 (1H,d,OH-3'), 5.32(2H,m,CH=CH), 4.45(1H,m,H-5'$_1$), 4.15(1H,m,H-5'$_2$), 3.98(1H,m,H-2'), 3.90(1H,m,H-3'), 3.88 (1H,m,H-4'), 2.33(2H,t,$CH_2$—COO), 1.95(4H,m,$CH_2$—CH=), 1.75(3H,s,$CH_3$-5), 1.52(2H,m,$CH_2$—C—COO), 1.25(20H,m,$CH_2$), 0.95(3H,t,$CH_3$—$CH_2$).

$^{13}$C NMR (DMSO-$d_6$, 75 MHz)δ: 172.78(COO), 163.78 (CO-4), 150.38(CO-2), 137.87(C-6), 129.56(CH=CH), 107.21(C-5), 85.31(C-1'), 81.73(C4'), 76.07(C-3'), 74.65(C-2'), 63.24(C-5'), 33.41, 31.10, 29.05, 28.81, 28.74, 28.64, 28.50, 28.34, 28.24, 26.56, 26.52, 24.43, 22.04($CH_2$), 13.85 ($CH_3$—$CH_2$), 12.15($CH_3$-5).

EXAMPLE 7

5'-O-(trans-11"-Octadecenoyl)1-β-D-Arabinofuranosyl-Thymine

To a solution of ARA-T (1.0 g, $3.87 \times 10^{-3}$ mol) in 20 ml anhydrous pyridine and 10 ml N,N-dimethylformamide was added 2 ml of a stock solution of trans-11-Octadecenoylchloride (2.1 g, $6.98 \times 10^{-3}$ mol) in 6 ml dichloromethane, and the reaction mixture was stirred under nitrogen at room temperature. The reaction was completed in the usual manner and crude product was recrystallized to give 1.3 g (65%) of the tide compound as a white solid.

$^1$H NMR (DMSO-$d_6$, 300 MHz)δ: 11.25(1H,s,N—H), 7.35(1H,s,H-6), 6.05(1H,d,H-1'), 5.65(1H,d,OH-2'), 5.55

(1H,d,OH-3'), 5.35(2H,m,HC=CH), 4.45(1H,m,H-5'$_1$), 4.15(1H,m,H-5'$_2$), 4.05(1H,m,H-2'), 3.95–3.90(2H,m,H-3' and H-4'), 2.35(2H,t,CH$_2$—COO), 1.95(4H,m,CH$_2$—CH=), 1.75(3H,s,CH$_3$-5), 1.52(2H,m,CH$_2$—C—COO), 1.25(20H,m,CH$_2$), 0.85(3H,t,CH$_3$—CH$_2$).

$^{13}$C NMR (DMSO-d$_6$, 75 MHz)δ: 172.75(COO), 163.79 (CO-4), 150.38(CO-2), 137.90(C-6), 129.98(CH=CH), 107.19(C-5), 85.34(C-1'), 81.77(C-4'), 76.11 (C-3'), 74.65 (C-2'), 63.26(C-5'), 33.42, 31.91, 31.10, 28.95, 28.83, 28.76, 28.65, 28.40, 28.37, 28.12, 24.44 and 22.04(CH$_2$), 13.83 (CH$_3$—CH$_2$), 12.13(CH$_3$-5).

EXAMPLE 8

5'-O-(cis-11"-Eicosenoyl)-1-β-D-Arabinofuranosyl-Thymine

To a solution of ARA-T (1.0 g, 3.87×10$^{-3}$ mol) in 20 ml anhydrous pyridine and 10 ml N,N-dimethylformamide was added 2 ml of a stock solution of cis-11-Eicosenoylchloride (2.1 g, 6.38×10$^{-3}$ mol) in 6 ml dichloromethane, and the reaction mixture was stirred under nitrogen at room temperature. The reaction was completed in the usual manner, and the crude product was purified on a column of silica gel with 10% methanol in chloroform as the eluent system. Homogeneous fractions were evaporated to give 1.25 g (58%) of the title compound as a white solid.

$^1$H NMR (DMSO d$_6$, 300 MHz)δ: 11.25(1H,s,N—H), 7.35(1H,s,H-6), 6.05(1H,d,H-1'), 5.65(1H,d,OH-2'), 5.55 (1H,d,OH-3'), 5.32(2H,m,CH=CH), 4.45(1H,m,H-5'$_1$), 4.15(1H,m,H-5'$_2$), 3.98(1H,m,H-2'), 3.90(1H,m,H-3'), 3.88 (1H,m,H-4'), 2.33(2H,t,CH$_2$—COO), 1.95(4H,m,CH$_2$—CH=), 1.75(3H,s,CH$_3$-5), 1.52(2H,m,CH$_2$—C—COO), 1.25(24H,m,CH$_2$), 0.95(3H,t,CH$_3$—CH$_2$).

$^{13}$C NMR (DMSO-d$_6$, 75 MHz)δ: 172.25(COO), 163.30 (CO-4), 149.89(CO-2), 137.38(C-6), 129.05(CH=CH), 106.71(C-5), 84.85(C-1'), 81.28(C4'), 75.60(C-3'), 74.16(C-2'), 62.76(C-5'), 32.92, 30.78, 28.58, 28.34, 28.19, 28.08, 27.88, 26.04, 23.95, 21.58(CH$_2$), 13.36(CH$_3$—CH$_2$), 11.65 (CH$_3$-5).

EXAMPLE 9

5'-O-(cis-13"-Docosenoyl)1-β-D-Arabinofuranosyl-Thymine

To a solution of ARA-T (1.0 g, 3.87×10$^{-3}$ mol) in 20 ml anhydrous pyridine and 10 ml N,N-dimethylformamide was added 2 ml of a stock solution of cis-13-Docosenoylchloride (2.15 g, 6.02×10$^{-3}$ mol) in 6 ml dichloromethane and the reaction mixture was stirred under nitrogen at room temperature. The reaction was completed and the product was purified on a column of silica gel (10% MeOH/CHCl$_3$) to give 1.15 g (51%) of the title compound as a white solid.

$^1$H NMR (DMSO-d$_6$, 300 MHz)δ: 11.25(1H,s,N—H), 7.35(1H,s,H-6), 6.05(1H,d,H-1'), 5.65(1H,d,OH-2'), 5.55 (1H,d,OH-3'), 5.32(2H,m,CH=CH), 4.45(1H,m,H-5'$_1$), 4.15(1H,m,H-5'$_2$), 3.98(1H,m,H-2'), 3.90(1H,m,H-3'), 3.88 (1H,m,H-4'), 2.33(2H,t,CH$_2$—COO), 1.95(4H,m,CH$_2$—CH=), 1.75(3H,s,CH$_3$-5), 1.52(2H,m,CH$_2$—C—COO), 1.25(28H,m,CH$_2$), 0.95(3H,t,CH$_3$—CH$_2$).

$^{13}$C NMR (DMSO-d$_6$, 75 MHz)δ: 172.63(COO), 163.84 (CO-4), 150.43(CO-2), 137.88(C-6), 129.44(CH=CH), 107.21(C-5), 85.51(C-1'), 81.92(C-4'), 76.20(C-3'), 74.69 (C-2'), 63.36(C-5'), 33.47, 31.40, 29.20, 29.15, 29.03, 28.83, 28.73, 28.55, 26.63, 24.50, 22.16(CH$_2$), 13.79(CH$_3$—CH$_2$), 12.14(CH$_3$-5).

EXAMPLE 10

9-(2'-(cis-9"-Hexadecenoyloxy)ethoxymethyl)-Guanine

To a solution of 9-(2-Hydroxyethoxymethyl)-Guanine (acyclovir, ACV) (1.0 g, 4.43×10$^{-3}$ mol) in 20 ml anhydrous pyridine and 10 ml N,N-dimethylformamide was added 2 ml of a stock solution of cis-9-Hexadecenoylchloride (4.29 g, 15.72×10$^{-3}$ mol) in 10 ml dichloromethane and the reaction mixture was stirred under nitrogen at room temperature. A further volume of 4 ml stock solution was added in 2 ml portions at approx. 10 hours intervals. After 60 hours total reaction time the solvents were removed at high vacuum and the residue was dilluted with 65 ml chloroform and 65 ml water. Centrifugation and recrystallization (ethanol) of the obtained semisolid mass gave 1.35 g (66%) of the title compound as a white solid.

$^1$H NMR (DMSO-d$_6$, 300 MHz)δ: 10.65(1H,s,NH), 7.82 (1H,s,CH-8), 6.50(2H,s,NH$_2$), 5.35(2H,s,CH$_2$-1'), 5.2–5.4 (2H,m,CH=CH), 4.07(2H,t,CH$_2$-4'), 3.65(2H,t,CH$_2$-3'), 2.21(2H,t,CH$_2$—COO), 1.98(4H,m,CH$_2$—CH=), 1.48(2H,m,CH$_2$—C—COO), 1.25(16H,m,CH$_2$), 0.85(3H,t,CH$_3$—CH$_2$).

$^{13}$C NMR (DMSO d$_6$, 75 MHz)δ: 172.72(COO), 156.79 (CO-6), 153.91(C-2), 151.41(C-4), 137.62(CH-8), 129.56 (CH=CH), 116.43(C-5), 71.81(CH$_2$-1'), 66.55(CH$_2$-3'), 62.53(CH$_2$-4'), 33.28, 31.14, 29.08, 28.54, 28.47, 28.40, 28.29, 26.59, 24.35, 22.07(CH2), 13.86(CH$_3$—CH$_2$).

EXAMPLE 11

9-(2'-(cis-6"-Octadecenoyloxy)ethoxymethyl)-Guanine

To a solution of ACV (1.0 g, 4.43×10$^{-3}$ mol) in 20 ml anhydrous pyridine and 10 ml N,N-Dimethylformamide was added 2 ml of a stock solution of cis-6Octadecenoylchloride (2.1 g, 6.98×10$^{-3}$ mol) in 6 ml dichloromethane and the reaction mixture was stirred under nitrogen at room temperature. The reaction was completed in the usual way and the product was recrystallized to give 1.6 g (80%) of the title compound as a white solid.

$^1$H NMR (DMSO-d$_6$, 300 MHz)δ: 10.65(1H,s,NH), 7.82 (1H,s,CH-8), 6.52(2H,s,NH$_2$), 5.25–5.4(4H,m,CH$_2$-1' and CH=CH), 4.07(2H,t,CH$_2$-4'), 3.65(2H,t,CH$_2$-3'), 2.25(2H,t,CH$_2$—COO), 1.95(4H,m,CH$_2$—CH=), 1.48(2H,m,CH,—C—COO), 1.20(20H,m,CH$_2$), 0.85(3H,t,CH$_3$—CH$_2$).

$^{13}$C NMR (DMSO-d$_6$, 75 MHz)δ: 172.66(COO), 156.72 (CO-6), 153.87(C-2), 151.37(C-4), 137.58(CH-8), 129.85 and 129.17(CH=CH). 116.42(C-5). 71.81(CH$_2$-1'), 66.52 (CH$_2$-3'). 62.52(CH$_2$-4'), 33.14, 31.25, 29.06, 28.97, 28.85, 28.66, 28.57, 28.43, 26.56, 26.26, 23.96, 22.05(CH$_2$), 13.88 (CH$_3$—CH$_2$).

EXAMPLE 12

9-(2'-(cis-9'-Octadecenoylcxy)ethoxymethyl)-Guanine

To a solution of ACV (2.0 g, 8.89×10$^{-3}$ mol) in 40 ml anhydrous pyridine and 20 ml N,N-Dimethylformamide was added 4 ml of a stock solution of cis-9-Octadecenoylchloride (4.25 g, 14.12×10$^{-3}$ mol) in 8 ml dichloromethane and the reaction mixture was stirred under nitrogen at room temperature. The remaining acid chloride solution was added in 4 ml portions each 8 hours. After a total of 40 hours reaction time the solvents were removed at high vacuum. The residue was suspended in 50 ml water and 100 ml chloroform. Centrifugation of the emulsion gave a semisolid mass that was recrystallized from ethanol to give 3.7 g (85%) of the title compound as a white solid.

'H NMR (DMSO-d$_6$, 300 MHz)δ: 10.65(1H,s,NH), 7.82 (1H,s,CH-8), 6.52(2H,s,NH$_2$), 5.25–5.4(4H,m,CH$_2$-1' and CH=CH), 4.07(2H,t,CH$_2$-4'), 3.65(2H,t,CH$_2$-3'), 2.25(2H, t,CH$_2$—COO), 1.95(4H,m,CH$_2$—CH=), 1.48(2H,m, CH$_2$—C—COO), 1.20(20H,m,CH$_2$), 0.85(3H,t,CH$_3$—CH$_2$).

$^{13}$C NMR (DMSO-d$_6$, 75 MHz)δ: 172.72(COO), 156.70 (CO-6), 153.85(C-2), 151.37(C4), 137.58(CH-8), 129.58 (CH=CH), 116.46(C-5), 71.76(CH$_2$-1'), 66.51(CH$_2$-3'), 62.50(CH$_2$-4'), 33.25, 31.23, 29.03, 28.78, 28.63, 28.54, 28.48, 28.42, 28.35, 26.54, 24.32, 22.03(CH$_2$), 13.87 (CH$_3$—CH$_2$).

EXAMPLE 13

9-(2'-(trans-9"-Octadecenoyloxy)ethoxymethyl)-Guanine

To a solution of ACV (2.0 g, 8.89×10$^{-3}$ mol) in 40 ml anhydrous pyridine and 20 ml N,N-dimethylformamide was added 4 ml of a stock solution of trans-9-Octadecenoylchloride (4.25 g, 14.12×10$^{-3}$ mol) in 8 ml dichloromethane and the reaction mixture was stirred under nitrogen at room temperature. The remaining acid chloride solution was added in 4 ml portions each 8 hours. After a total of 50 hours reaction time the solvents were removed at high vacuum. The residue was suspended in 50 ml water and 100 ml chloroform and centrifugation of the emulsion gave a semisolid mass that was recrystallized from ethanol to give 3.75 g (86%) of the title compound as a white solid.

$^1$H NMR (DMSO-d$_6$, 300 MHz)δ: 10.65(1H,s,NH), 7.82 (1H,s,CH-8), 6.75(2H,s,NH$_2$), 5.25–5.4(4H,m,CH$_2$, 1' and Ch=CH), 4.07(2H,t,CH$_2$-4'), 3.65(2H,t,CH$_2$-3'), 2.21(2H,t, CH$_2$—COO). 1.98(4H,m,CH$_2$—C=)1.45(2H,m,CH$_2$—C—COO), 1.25(20H,m,CH$_2$), 0.85(3H,t,CH$_3$—CH$_2$).

$^{13}$C NMR (DMSO-d$_6$, 75 MHz)δ: 172.77(COO), 156.72 (CO-6), 154.17(C-2), 151.36(C-4), 137.52(CH-8), 130.03 (CH=CH), 116.44(C-5), 71.77(CH$_2$-1'), 66.54(CH$_2$-3'), 62.55(CH$_2$-4'). 33.28, 31.93, 31.26, 28.98, 28.95, 28.82, 28.69, 28.49, 28.38, 28.33, 24.35 and 22.08(CH$_2$), 13.91 (CH$_3$—CH$_2$).

EXAMPLE 14

9-(2'-(cis-11"-Octadecenoyloxy)etioxymethyl)-Guanine

To a solution of ACV (1.0 g, 4.43×10$^{-3}$ mol) in 20 ml anhydrous pyridine and 10 ml N,N-Dimethylformamide was added 2 ml of a stock solution of cis-11-Octadecenoylchoride (2.1 g, 6.98×10$^{-3}$ mol) in 6 ml dichloromethane and the reaction mixture was stirred under nitrogen at room temperature. The reaction was completed in the usual way and the product was recrystallized to give 1.8 g (90%) of the title compound as a white solid.

$^1$H NMR (DMSO-d$_6$, 300 MHz)δ: 10.65(1H,s,NH), 7.82 (1H,s,CH-8), 6.52(2H,s,NH$_2$), 5.25–5.4(4H,m,CH$_2$-1' and CH=CH), 4.07(2H,t,CH$_2$-4'), 3.65(2H,t,CH$_2$-3'), 2.25(2H, t,CH$_2$—COO), 1.95(4H,m,CH$_2$—CH=), 1.48(2H,m, CH$_2$—C—COO), 1.20(20H,m,Ch$_2$), 0.85(3H,t,CH$_3$—CH$_2$).

$^{13}$C NMR (DMSO-d$_6$, 75 MHz)δ: 172.74(COO), 156.62 (CO-6), 153.91(C-2), 151.34(C4), 137.58(CH-8), 129.58 (CH=CH), 116.22(C-5), 71.82(CH$_2$-1'), 66.55(CH$_2$-3'), 62.50(CH$_2$-4'), 33.26, 31.09, 29.06, 28.81, 28.79, 28.62, 28.54, 28.36, 28.23, 26.55, 24.33, 22.04(CH$_2$), 13.87 (CH$_3$—CH$_2$).

EXAMPLE 15

9-(2'-(trans-11"-Octadecenoyloxy)ethoxymethyl)-Guanine

To a solution of ACV (1.0 g, 4.43×10$^{-3}$ mol) in 20 ml anhydrous pyridine and 10 ml N,N-dimethylformamide was added 2 ml of a stock solution of trans-11-Octadecenoylchloride (2.1 g, 6.98×10$^{-3}$ mol) in 6 ml dichloromethane, and the reaction mixture was stirred under nitrogen at room temperature. The reaction was completed in the usual way and the crude product was recrystallized to give 1.7 g (78%) of the title compound as a white solid.

$^1$H NMR (DMSO-d$_6$, 300 MHz)δ: 10.60(1H,s,NH), 7.81 (1H,s,CH-8), 6.60(2H,s,NH$_2$), 5.25–5.4(4H,m,CH$_2$-1' and CH=CH), 4.05(2H,t,CH$_2$-4'), 3.65(2H,t,CH$_2$-3'), 2.22(2H, t,CH$_2$—COO), 1.95(4H,m,CH$_2$—CH=), 1.45(2H,m, CH$_2$—C—COO), 1.20(20H,m,CH$^2$), 0.85(3H,t,CH$_3$—CH$_2$).

$^{13}$C NMR (DMSO-d$_6$, 75 MHz)δ: 172.75(COO), 156.76 (CO-6), 153.87(C-2), 151.41(C-4), 137.63(CH-8), 130.03 (CH=CH), 116.48(C-5), 71.79(CH$_2$-1'), 66.54(CH$_2$-3'), 62.52(Ch$_2$-4'), 33.29. 31.92, 31.09, 28.95, 28.79, 28.63, 28.38, 28.12, 24.35 and 22.05(CH$_2$), 13.86(CH$_3$—CH$_2$).

EXAMPLE 16

9-(2'-(cis-11"-Eicosenoyloxy)ethoxymethyl)-Guanine

To a solution of ACV(1.0 g, 4.43×10$^{-3}$ mol) in 20 ml anhydrous pyridine and 10 ml N,N-dimethylformamide was added 2 ml of a stock solution of cis-11-Eicosenoylchloride (1.59 g, 4.83×10$^{-3}$ mol) in 4 ml dichloromethane, and the reaction mixture was stirred under nitrogen at room temperature. The remaining acid chloride solution was added in 1 ml portions each 8 hours. After a total of 60 hours reaction time the solvents were removed at high vacuum. The residue was treated with chloroform and water and finally purified on a column of silica gel (10% MeOH/CHCl$_3$) to give 0.92 g (40%) of the title compound as a white solid.

$^1$H NMR (DMSO-d$_6$, 300 MHz)δ: 10.65(1H,s,NH), 7.81 (1H s,CH-8), 6.50(2H,s,NH$_2$), 5.25–5.4(4H,m,CH$_2$-1' and CH=CH), 4.08(2H,t,CH$_2$-4'), 3.65(2H,t,CH$_2$-3'), 2.21(2H, t,CH$_2$—COO), 2.0(4H,m,CH$_2$—C=), 1.45(2H,m,CH$_2$—C—COO), 1.25(24H,m,CH$_2$), 0.85(3H,t,CH$_3$—CH$_2$).

$^{13}$C NMR (DMSO-d$_6$, 75 MHz)δ: 172.73(COO), 156.70 (CO-6), 153.90(C-2), 151.37(C-4), 137.59(CH-8), 129.58 (CH=CH), 116.35(C-5), 71.81(CH$_2$-1'), 66.54(CH$_2$-3'), 62.52(CH$_2$-4'), 33.28, 31.26, 29.09, 28.82, 28.67, 28.58, 28.40, 26.56, 24.35 and 22.07(CH$_2$), 13.88(CH$_3$—CH$_2$).

EXAMPLE 17

9-(2'-(cis-13"-Docosenoyloxy)ethoxymethyl)-Guanine

To a solution of ACV (1 g, 4.43×10$^{-3}$ mol) in 20 ml anhydrous pyridine and 10 ml N,N-diethylformamide was added 2 ml of a stock solution of cis-13-Docosenoylchloride (2.10 g, 5.88×10$^{-3}$ mol) in 6 ml dichloromethane and the reaction mixture was stirred under nitrogen at room temperature. The react ion was completed and the product was recrystallized (ethanol) to give 0.24 g (52%) of the title compound as a white solid.

$^1$H NMR (DMSO-d$_6$, 300 MHz)δ: 10.65(1H,s,NH). 7.80 (1H,s,CH-8), 6.50(2H,s,NH$_2$), 52–5.4(4H,m,CH$_2$-1', CH=CH), 4.10(2H,t,CH$_2$-4'), 3.65(2H,t,CH$_2$-3'), 2.22(2H, t,Ch$_2$—COO), 2.05(4H,m,CH$_2$-C=), 1.45(2H,m,CH$_2$—C—COO), 1.25(28H,m,CH$_2$) 0.85(3H,t,CH$_3$—CH$_2$).

$^{13}$C NMR (DMSO-d$_6$, 75 MHz)δ: 172.74(COO), 156.70 (CO-6), 153.87(C-2), 151.38(C-4), 137.58(CH-8), 129.60 (CH=CH), 116.45(C-5), 71.78(CH$_2$-1'), 66.53(CH$_2$-3'), 66.52(CH$_2$-4'), 33.28, 31.25, 29.06, 28.98, 28.85, 28.66, 28.56, 28.39, 26.53, 24.35, 22.06(CH$_2$), 13.89(CH$_3$—CH$_2$).

EXAMPLE 18

5'-O-(cis-9"-Octadecenoyl)-3'-deoxy-3'-azido-Thymidine

To a solution of 3'-deoxy-3'-azido-Thymidine (AZT) (1.0 g, $3.75 \times 10^{-3}$ mol) in 20 ml anhydrous pyridine was added 2 ml of a stock solution of cis-9-Octadecenoylchloride (70%, 1.7 g, $3.9 \times 10^{-3}$ mol) in 6 ml dichloromethane, and the reaction mixture was stirred under nitrogen at room temperature. The remaining stock solution was added in 2 ml portions at approx. 8 hours intervals. After a total of 60 hours reaction time, the solvents were evaporated at high vacuum and the residue diluted with chloroform 100 ml and water 50 ml. The organic phase was treated with brine, dried ($MgSO_4$) and concentrated to give a viscous oil. The product was purified on a column of silica gel with 3% methanol in chloroform as eluent system. Homogenous fractions were evaporated to give 1.65 g (82%) of the title compound as a colorless viscous oil.

$^1$H NMR (DMSO-$d_6$, 300 MHz)δ: 11.25(1H,s,NH), 7.45 (1H,s,H-6), 6.12(1H,t,H-1'), 5.25–5.4(2H,m,CH=CH), 4.45(1H,m,H-3'), 4.25(2H,m,H-5'), 3.95(1H,m,H-4'), 2.25–2.45(2H,m,$CH_2$-2'), 2.35(2H,t,$CH_2$—COO), 1.97(4H, m,$CH_2$—CH=), 1.77(3H,s,$CH_3$-5), 1.53(2H,m,$CH_2$—C—COO), 1.25(20H,m,$CH_2$), 0.85(3H,t,$CH_3$—$CH_2$).

$^{13}$C NMR (DMSO-$d_6$, 75 MHz)δ: 172.51(COO), 163.58 (CO-4), 150.32(CO-2), 135.91(CH-6), 129.55 and 129.49 (CH=CH), 109.81(C-5), 83.61(CH-1'), 80.61(CH-3'), 63.11($CH_2$-5'), 60.17(CH4'), 35.67($CH_2$-2'), 33.30, 31.29, 29.10, 29.06, 28.85, 28.70, 28.61, 28.54, 28.43, 26.56, 24.30, 22.09($CH_2$), 13.85($CH_3$—$CH_2$), 12.04($CH_3$-5).

EXAMPLE 19

5'-O-(cis-9"-Octadecenoyl)-9-β-D-Arabinofuranosyl-Adenine

To a solution of 9-β-D-Arabinofuranosyl-Adenine (ARA-A) (1.0 g, $3.74 \times 10^{-3}$ mol) in 10 ml anhydrous pyridine and 20 ml N,N,dimethylformamide was added 2 ml of a stock solution of cis-9-Octadecenoylchloride (2.1 g, $6.98 \times 10^{-3}$ mol) in 6 ml dichloromethane, and the reaction mixture was stirred under nitrogen at room temperature. The remaining stock solution was added in 2 ml portions at approx. 8 hours intervals. After a total of 50 hours reaction time the solvents were removed at high vacuum and the residue was dissolved in 10% methanol in chloroform and filtered through a small silica gel column. The concentrated product fractions were purified on a silica gel column to give 0.6 g (30%) of the title compound as a white solid.

$^1$H NMR (DMSO-$d_6$, 300 MHz)δ: 8.18(1H,s,ArH), 8.12 (1H,s,ArH), 7.25(2H,s,$NH_2$), 6.30(1H,d,H-1'), 5.78(1H,d, OH-2'), 5.68(1H,d,OH-3'), 5.2–5.4(2H,m,CH=CH), 4.38 (1H,m,H-5'$_1$), 4.25(1H,m,H-5'$_2$), 4.15(2H,m,H-2', H-3'), 3.95(1H,m,H-4'), 2.30(2H,t,$CH_2$—COO), 1.95(4H,m, $CH_2$—C=), 1.50(2H,m,$CH_2$—C—COO), 1.25(20H,m, $CH_2$), 0.85(3H,t,$CH_3$—$CH_2$).

$^{13}$C NMR (DMSO-$d_6$, 75 MHz)δ: 172.73(COO), 155.43 (C-6), 151.85(C-2), 149.28(C4), 140.60(C-8), 129.66 and 129.54(CH=CH). 118.22(C-5), 83.82(C-1'), 81.23(C-4'), 75.88(C-2'), 75.11(C-3'), 63.88(C-5'), 33.37, 31.29, 29.09, 29.05, 28.85, 28.70, 28.59, 28.48, 28.42, 26.56, 24.41, 22.08($CH_2$), 13.87($CH_3$—$CH_2$).

EXAMPLE 20

5'-O-(trans-9"-Octadecenoyl)-1-β-D-Arabinofuranosyl-(N6-methyl)-Adenine

To a solution of 9-β-D-Arabinofuranosyl-N-6-methyl-Adenine (1.0 g, $3.55 \times 10^{-3}$ mol) in 10 ml anhydrous pyridine and 15 ml N,N-dimethylformamide was added 2 ml of a stock solution of trans-9-Octadecenoylchloride (2.0 g, $6.64 \times 10^{-3}$ mol) in 6 ml dichloromethane, and the reaction mixture was stirred under nitrogen at room temperature. The remaining stock solution was added in 2 ml portions at approx. 8 hours intervals. After a total of 60 hours reaction time the solvents were removed at high vacuum and the residue was dissolved in 5% methanol in chloroform and repeatedly chromatographed on a column of silica gel to yield 0.7 g (36%) of the title compound as a white solid.

$^1$H NMR (DMSO-$d_6$, 300 MHz)δ: 8.25(1H,s,ArH), 8.10 (1H,s,ArH), 7.75(1H,s,NH), 6.29(1H,d,H-1'), 5.78(1H,d, OH-2'), 5.70(1H,d,OH-3'), 5.25–5.35(2H,m,CH=CH), 4.40 (1H,m,H-5'$_1$), 4.27(1H,m,H-5'$_2$), 4.15(2H,m,H-2',H-3'), 3.95(1H,m,H-4'), 2.95(3H,br,s,N—$CH_3$), 2.30(2H,t,$CH_2$—COO), 1.90(4H,m,$CH_2$—C=),1.50(2H,m,$CH_2$—C—COO), 1.25(20H,m,$CH_2$), 0.85(3H,t,$CH_3$—$CH_2$).

$^{13}$C NMR (DMSO-$d_6$, 75 MHz)δ: 172.75(COO), 154.89 (C-6), 152.43(C-2), 149.33(C-4), 140.02(C-8), 129.99 (CH=CH), 118.20(C-5), 83.61(C-1'), 81.06(C-4'), 75.77(C-2'), 75.06(C-3'), 63.76(-5'), 33.36, 31.90, 31.25, 28.97, 28.90, 28.81, 28.68, 28.47, 28.36, 28.30($CH_2$), 27.20(N—$Ch_3$), 24.41, 22.07($CH_2$), 13.89($CH_3$—$CH_2$).

EXAMPLE 21

9-(4'-(trans-9"-Octadecenoyloxy)3'-hydroxymethyl-butyl)-Guanine

To a solution of 9(4-hydroxy-3-hydroxymethyl-butyl) guanine (Penciclovir) (1.0 g, $3.98 \times 10^{-3}$ mol) in 10 ml anhydrous pyridine and 40 ml N,N-dimethylformamide was added 2 ml of a stock solution of trans-9-Octadecenoylchloride (2.1 g, $6.98 \times 10^{-3}$ mol) in 6 ml dichloromethane, and the reaction mixture was stirred under nitrogen at room temperature. The remaining stock solution was added in 2 ml portions at approx. 8 hours intervals. After a total of 65 hours reaction time the solvents were removed at high vacuum and the residue was dissolved in 15% methanol in chloroform and eluted through a silica gel column. Homogenous fractions were recrystallized from ethanol to give 0.45 g (22%) of the title compound as a white solid.

$^1$H NMR (DMSO-$d_6$, 300 MHz)δ: 10.50(1H,s,NH), 7.65 (1H,s,CH-8), 6.43(2H,s,$NH_2$), 5.33(2H,m,CH=CH), 4.62 (1H,t,OH), 4.00(4H,m,$CH_2$—N and $RCOOCH_2$), 3.38(2H, m,$CH_2$—OH). 2.25(2H,t,$CH_2$—COO), 1.90(4H,m,$CH_2$—C=), 1.60–1.80(CH and C$\underline{H}_2$—$CH_2$N), 1.45(2H,m,C$\underline{H}_2$—C—COO), 1.20(20H,m,$CH_2$), 0.85(3H,t,$CH_3$).

$^{13}$C NMR (DMSO-$d_6$, 75 MHz)δ: 172.90(COO), 156.75 (C-6), 153.40(C-2), 151.07(C-4), 137.22(C-8), 130.02 (CH=CH), 116.57(C-5), 63.80(RCOO$\underline{C}H_2$), 60.50 ($CH_2OH$), 40.67($CH_2N$), 37.54(CH), 33.44, 31.88, 31.22, 28.95, 28.90, 28.77, 28.64, 28.43, 28.27, 24.38, 22.04($CH_2$), 13.90($CH_3$).

EXAMPLE 22

9-(2'-(trans-9"-Octadecenoyloxy)-1'-hydroxymethyl-ethoxymethyl)-Guanine

To a solution of 9-{[2-Hydroxy-1-(hydroxy]methyl) ethoxymethyl}guanine (ganciclovir) (0.655 g, $2.56 \times 10^{-3}$ mol) in 10 ml anhydrous pyridine and 40 ml N,N-dimethylacetamide was added 2 ml of a stock solution of trans-9-Octadecenoylchloride (1.3 g, $4.32 \times 10^{-3}$ mol) in 6 ml dichloromethane, and the reaction mixture was stirred under nitrogen at 40° C. The remaining stock solution was added in 2 ml portions at approx. 10 hours intervals. After a total of 60 hours reaction time the solvents were removed at high vacuum. The residue was suspended in 100 ml water and 100 ml dichloromethane and centrifugation of the emulsion gave a semisolid mass that was recrystallized from ethanol to give 0.8 g (60%) of the title compound as a white solid.

$^1$H NMR (DMSO-$d_6$, 300 MHz)δ: 10.60(1H,s,NH), 7.81 (1H,s,CH-8), 6.58(2H,s,$NH_2$), 5.45(2H,s,$OCH_2$N), 5.35 (2H,m,CH=CH), 4.85(1H,t,OH), 4.08(1H,m) 3.90(1H,m) and 3.75(1H,m)($RCOOCH_2$ and CH—O). 3.35(2H,m, $CH_2OH$), 2.08(2H,t,$CH_2$—COO), 1.93(4H,m,$CH_2$—C=), 1.10–1-45(22H,m,$CH_2$), 0.85(3H,t,$CH_2$—$CH_2$).

$^{13}$C NMR (DMSO-$d_6$, 75 MHz)δ: 172.64(COO), 156.85 (C-6), 153.84(C-2), 151.34(C-4), 137.62(C-8), 130.02 (CH=CH), 116.48(C-5), 76.88(CH—O), 71.29($OCH_2$N), 63.13(RCOO$\underline{C}H_2$). 60.39($CH_2$OH), 33.19, 31.97, 31.29, 29.02, 28.85, 28.72, 28.53, 28.41, 27.07, 27.02, 24.32, 22.10($CH_2$), 13.90($CH_3$).

What is claimed is:

1. A pharmaceutical composition for the treatment of viral infections comprising a monoester pharmaceutical composition of formula I:

Nu-O-Fa wherein O is an oxygen, Nu is a nucleoside or nucleoside analogue, excluding adenosine, cytidine, guanosine, thymidine, 2'-deoxyadenosine, 2'-deoxycytidine, 2'-deoxyguanosine, and uridine, and Fa is an acyl group of a mono-unsaturated C18 or C20 ω-9 fatty acid, which fatty acid is esterified with a hydroxyl group in the 5'-position of the sugar moiety of the nucleoside or nucleoside analogue or with a hydroxyl group on the non-cyclic chain of the nucleoside analogue, wherein Nu-O-Fa is not 5'-O-oleyl-ara-cytidine or 2,2'-anhydro-5'-O-oleyl-ara-cytidine, and a pharmaceutically acceptable carrier or excipient.

2. The pharmaceutical composition of claim 1, wherein Nu is represented by Formula II

S—B wherein S is a moiety selected from the group consisting of:

1-β-D-arabinofuranose, 2,3-di-deoxy-3-azido-1-β-D-ribofuranose, 2-hydroxy-ethoxy-methyl, 4-hydroxy-3-(hydroxymethyl)-butyl, 2-hydroxy-1-(hydroxymethyl)-ethoxy-methyl and 2,3-di-hydroxy-propoxy; B is a heterocyclic base selected from the group consisting of adenine, guanine, cytosine, uracil, thymine, 5-trifluoromethyluracil, and 5-trideuteriomethyluracil; wherein when B is a purine, S is attached at the N-9 position, and when B is a pyrimidine, S is attached at the N-1 position.

3. The pharmaceutical composition of claim 2, wherein Nu is arabinofuranosyl thymine (Ara T), arabinofuranosyl adenine (Ara A), acyclovir (ACV), 3'-azidothymidine (AZT), a purine arabinoside of the general formula

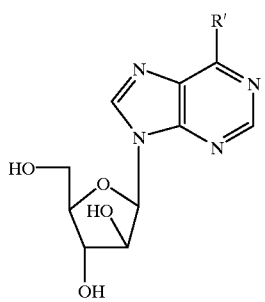

wherein R' is $NH_2$, $NHCH_3$, $N(CH_3)_2$ or $OCH_3$, or a nucleoside analogue of the general formula:

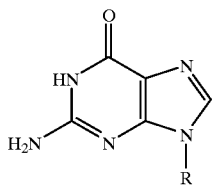

wherein R is a non-cyclic group containing at least one hydroxyl group.

4. The pharmaceutical composition of claim 3, wherein R is [2-hydroxy-1-(hydroxymethyl)ethoxy]methyl.

5. The pharmaceutical composition of any one of claims 1 through 4 wherein Fa is oleic acid, elaidic acid, or cis- or trans-eicosenic acid.

6. The pharmaceutical composition of claim 1, wherein Nu is acyclovir and Fa is oleic acid.

7. The pharmaceutical composition of claim 1, wherein Nu is acyclovir and Fa is elaidic acid.

8. The pharmaceutical composition of claim 1, wherein Nu is acyclovir and Fa is cis- or trans-eicosenic acid.

9. The pharmaceutical composition of claim 1, wherein Nu is Ara T and Fa is elaidic acid.

10. The pharmaceutical composition of claim 1, wherein Nu is Ara T and Fa is oleic acid.

11. The pharmaceutical composition of claim 1, wherein Nu is Ara T and Fa is cis- or trans-eicosenic acid.

12. The pharmaceutical composition of claim 1, wherein Nu is Ara A and Fa is cis- or trans-eicosenic acid.

13. The pharmaceutical composition of claim 1, wherein Nu is Ara A and Fa is oleic acid.

14. The pharmaceutical composition of claim 1, wherein Nu is Ara A and Fa is elaidic acid.

15. The pharmaceutical composition of claim 1, wherein Nu is ganciclovir and Fa is elaidic acid.

16. The pharmaceutical composition of claim 1, wherein Nu is AZT and Fa is elaidic acid.

17. The pharmaceutical composition of claim 1, wherein Nu is AZT and Fa is oleic acid.

18. The pharmaceutical composition of claim 1, wherein Nu is AZT and Fa is cis- or trans-eicosenic acid.

19. A pharmaceutical composition according to claim 1, for the treatment of HIV infections, wherein Nu is AZT and Fa is selected from the group consisting of elaidic acid, oleic acid, and cis- or trans-eicosenic acid.

20. A pharmaceutical composition according to claim 1, for the treatment of HSV 1 or 2 infections, wherein Nu is acyclovir and Fa is selected from the group consisting of oleic acid, elaidic acid, and cis- or trans-eicosenic acid.

21. A pharmaceutical composition according to claim 1, for the treatment of hepatitis B infections, wherein Nu is selected from the group consisting of Ara T and Ara A and Fa is selected from the group consisting of oleic acid, elaidic acid, and cis- or trans-eicosenic acid.

22. A method of preparing a pharmaceutical composition for the treatment of a viral infection, comprising the steps of
(a) selecting a monoester pharmaceutical composition of formula I:

Nu-O-Fa wherein O is an oxygen, Nu is a nucleoside or nucleoside analogue, excluding adenosine, cytidine, guanosine, thymidine, 2'-deoxyadenosine, 2'-deoxycytidine, 2'-deoxyguanosine, and uridine, and Fa is an acyl group of a mono-unsaturated C18 or C20 ω-9 fatty acid, which fatty acid is esterified with a hydroxyl group in the 5'-position of the sugar moiety of the nucleoside or nucleoside analogue or with a hydroxyl group on the non-cyclic chain of the nucleoside analogue; wherein Nu-O-Fa is not 5'-O-oleyl-ara-cytidine or 2,2'-anhydro-5'-O-oleyl-ara-cytidine, and
(b) combining the compound with a pharmaceutically acceptable carrier or excipient.

23. A method for treatment of a patient suffering from a viral infection wherein a monoester pharmaceutical composition of formula I:

Nu-O-Fa wherein O is an oxygen, Nu is a nucleoside or nucleoside analogue, excluding adenosine, cytidine, guanosine, thymidine, 2'-deoxyadenosine, 2'-deoxycytidine, 2'-deoxyguanosine, and uridine, and Fa is an acyl group of a mono-unsaturated C18 or C20 ω-9 fatty acid, which fatty acid is esterified with a hydroxyl group in the 5'-position of the sugar moiety of the nucleoside or nucleoside analogue or with a hydroxyl group on the non-cyclic chain of the nucleoside analogue; wherein Nu-O-Fa is not 2,2'-anhydro-5'-O-oleyl-ara-cytidine, is administered.

24. A method for the treatment of a patient with a viral infection caused by a hepatitis B virus wherein a monoester pharmaceutical composition of formula I:

Nu-O-Fa wherein O is an oxygen, Nu is a nucleoside or nucleoside analogue, excluding adenosine, cytidine, guanosine, thymidine, 2'-deoxyadenosine, 2'-deoxycytidine, 2'-deoxyguanosine, and uridine, and Fa is an acyl group of a mono-unsaturated C18 or C20 ω-9 fatty acid, which fatty acid is esterified with a hydroxyl group in the 5'-position of the sugar moiety of the nucleoside or nucleoside analogue or with a hydroxyl group on the non-cyclic chain of the nucleoside analogue; wherein Nu-O-Fa is not 2,2'-anhydro-5'-O-oleyl-ara-cytidine, in combination with an interferon, is administered.

25. A monoester pharmaceutical composition of formula I:

Nu-O-Fa wherein O is an oxygen, Nu is a nucleoside or nucleoside analogue, excluding adenosine, cytidine, guanosine, thymidine and uridine, and Fa is an acyl group of a mono-unsaturated C18 or C20 ω-9 fatty acid, which fatty acid is esterified with a hydroxyl group in the 5'-position of the sugar moiety of the nucleoside or nucleoside analogue or with a hydroxyl group on the non-cyclic chain of the nucleoside analogue, wherein Nu is represented by Formula II

S—B wherein S is a moiety selected from the group consisting of: 1-β-D-arabinofuranose, 2,3-di-deoxy-3-azido-1-β-D-ribofuranose, 2-hydroxy-ethoxy-methyl, 4-hydroxy-3-(hydroxymethyl)-butyl, 2-hydroxy-1-(hydroxy-methyl)-ethoxy-methyl and 2,3-di-hydroxy-propoxy; and B is a heterocyclic base selected from the group consisting of adenine, guanine, cytosine, uracil, thymine, 5-trifluoromethyluracil, and 5-trideutriomethyluracil; wherein when B is a purine, S is attached at the N-9 position, and when B is a pyrimidine, S is attached at the N-1 position.

26. The pharmaceutical composition of claim 25, wherein Nu is arabinofuranosyl thymine (Ara-T), arabinofuranosyl adenine (Ara A), acyclovir (ACV), 3'-azidothymidine (AZT), a purine arabinoside of the general formula

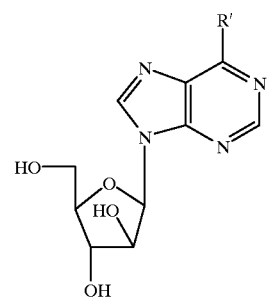

wherein R' is $NH_2$, $NHCH_3$, $N(CH_3)_2$ or $OCH_3$, or a nucleoside analogue of the general formula:

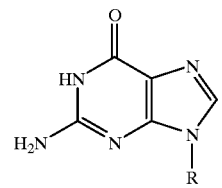

wherein R is a non-cyclic group containing at least one hydroxyl group.

27. The compound of claim 26, wherein R is [2-hydroxy-1-(hydroxymethyl)ethoxy]methyl.

28. The compound of any one of claims 25 through 27 wherein Fa is oleic acid, elaidic acid, or cis- or trans-eicosenic acid.

29. The compound of claim 25, wherein Nu is acyclovir and Fa is oleic acid.

30. The compound of claim 25, wherein Nu is acyclovir and Fa is elaidic acid.

31. The compound of claim 25, wherein Nu is acyclovir and Fa is cis- or trans-eicosenic acid.

32. The compound of claim 25, wherein Nu is Ara T and Fa is elaidic acid.

33. The compound of claim 25, wherein Nu is Ara T and Fa is oleic acid.

34. The compound of claim 25, wherein Nu is Ara T and Fa is cis- or trans-eicosenic acid.

35. The compound of claim 25, wherein Nu is Ara A and Fa is cis- or trans-eicosenic acid.

36. The compound of claim 25, wherein Nu is Ara A and Fa is oleic acid.

37. The compound of claim 25, wherein Nu is Ara A and Fa is elaidic acid.

38. The compound of claim 25, wherein Nu is ganciclovir and Fa is elaidic acid.

39. The compound of claim 25, wherein Nu is AZT and Fa is elaidic acid.

40. The compound of claim 25, wherein Nu is AZT and Fa is oleic acid.

41. The compound of claim 25, wherein Nu is AZT and Fa is cis- or trans-eicosenic acid.

42. In a method of increasing the therapeutic effectiveness of an antiviral nucleoside or nucleoside analogue by esterifying said nucleoside or nucleoside analogue with an unsaturated fatty acid, said esterification being at the 5' position of the sugar moiety if a nucleoside is used, and being at a hydroxyl group on the non-cyclic chain if a nucleoside analogue is used, the improvement wherein the unsaturated fatty acid that is used is a mono-unsaturated $C_{18}$ or $C_{20}$ fatty acid selected from the group consisting of oleic acid, elaidic acid, cis-eicosenic acid, and trans-eicosenic acid.

43. In a method of treating a patient having a viral infection by administering to the patient a therapeutically effective amount of an antiviral nucleoside or nucleoside analogue, the improvement wherein the nucleoside or nucleoside analogue is in the form of an ester with a mono-unsaturated $C_{18}$ or $C_{20}$ fatty acid selected from the group consisting of oleic acid, elaidic acid, cis-eicosenic acid, and trans-eicosenic acid, the esterification being at the 5'-position of the sugar moiety if a nucleoside is used and being with a hydroxyl group on the non-cyclic chain if a nucleoside analogue is used.

* * * * *